(12) United States Patent
Baker et al.

(10) Patent No.: US 11,626,033 B2
(45) Date of Patent: Apr. 11, 2023

(54) PREFILLED SYRINGE PLUNGER SIMULATION TRAINING DEVICE

(71) Applicants: NOBLE INTERNATIONAL, INC., Orlando, FL (US); Dinesh Venkata Koka, Winter Park, FL (US)

(72) Inventors: Jeff Baker, Orlando, FL (US); Dinesh Venkata Koka, Winter Park, FL (US); Tingting Liu, Orlando, FL (US); Joseph Reynolds, Orlando, FL (US); Matthew Palyo, Orlando, FL (US); Robert Anderson, Winter Park, FL (US); Jeffery A. Lettman, Orlando, FL (US); Joshua Hopkins, Casselberry, FL (US)

(73) Assignee: NOBLE INTERNATIONAL, INC., Orlando, FL (US)

( * ) Notice: Subject to any disclaimer, the term of this patent is extended or adjusted under 35 U.S.C. 154(b) by 523 days.

(21) Appl. No.: 16/499,529

(22) PCT Filed: Mar. 29, 2018

(86) PCT No.: PCT/US2018/025290
§ 371 (c)(1),
(2) Date: Sep. 30, 2019

(87) PCT Pub. No.: WO2018/183772
PCT Pub. Date: Oct. 4, 2018

(65) Prior Publication Data
US 2020/0410897 A1    Dec. 31, 2020

Related U.S. Application Data

(60) Provisional application No. 62/478,101, filed on Mar. 29, 2017, provisional application No. 62/545,734, filed on Aug. 15, 2017.

(51) Int. Cl.
G09B 23/28      (2006.01)
A61M 5/31      (2006.01)
A61M 5/315     (2006.01)

(52) U.S. Cl.
CPC ......... G09B 23/285 (2013.01); A61M 5/3148 (2013.01); A61M 5/31501 (2013.01);
(Continued)

(58) Field of Classification Search
CPC .............. G09B 23/285; A61M 5/3148; A61M 5/31501; A61M 5/31513; A61M 2005/3128; A61M 2005/3151
(Continued)

(56) References Cited

U.S. PATENT DOCUMENTS 6,213,985 B1    4/2001   Niedospial, Jr.
9,336,690 B2    5/2016   Helmer et al.
(Continued)

FOREIGN PATENT DOCUMENTS

EP      2784766 A1    10/2014
WO   2016123144 A2    8/2016
WO   2017027753 A1    2/2017

OTHER PUBLICATIONS

EP18777514.3 EESR; dated Dec. 21, 2020; 7 pages.
PCT/US2018/025290; International Search Report and Written Opinion, dated Sep. 18, 2018, 24 pages.

*Primary Examiner* — Robert P Bullington
(74) *Attorney, Agent, or Firm* — Timothy H. Van Dyke; Wolter, Van Dyke, Davis, PLLC

(57) ABSTRACT

In an embodiment, an injection simulation device is provided including a housing defining a channel, the housing comprising a proximal end and a distal end, a plunger comprising a plunger rod body having a proximal end and a distal end and a stopper disposed at the distal end of the plunger rod, the plunger movable proximally and distally (Continued)

within the channel; and a friction feature associated with the housing, the friction feature for interfacing with the plunger rod, wherein the plunger moves in a distal direction relative to the housing to simulate medicament delivery and in a proximal direction to reset the injection simulation device, wherein the friction feature optionally causes differential resistance on the plunger rod, when the plunger rod moves in either the distal or proximal direction.

18 Claims, 36 Drawing Sheets

(52) U.S. Cl.
CPC . *A61M 5/31513* (2013.01); *A61M 2005/3128* (2013.01); *A61M 2005/3151* (2013.01)

(58) Field of Classification Search
USPC .......................................................... 434/262
See application file for complete search history.

(56) References Cited

U.S. PATENT DOCUMENTS

| | | |
|---|---|---|
| 2004/0127859 A1 | 7/2004 | Ward |
| 2006/0253074 A1 | 11/2006 | Thayer |
| 2015/0235571 A1 | 8/2015 | Alexandersson |
| 2016/0293058 A1 | 10/2016 | Gaillot et al. |
| 2016/0335920 A1* | 11/2016 | Bendek ................. G09B 23/285 |
| 2017/0004737 A1 | 1/2017 | Baker et al. |

* cited by examiner

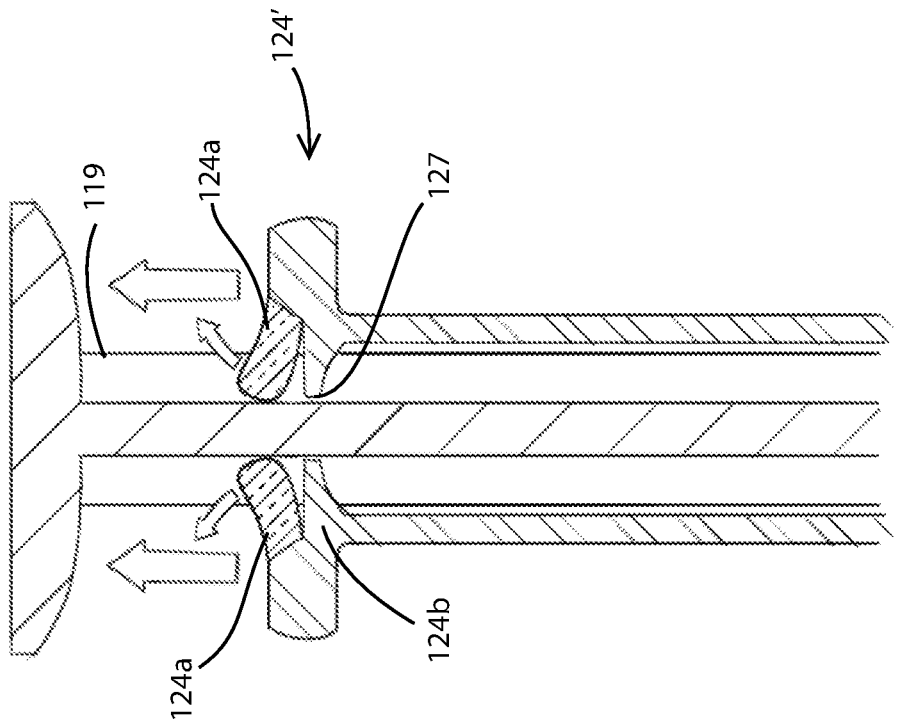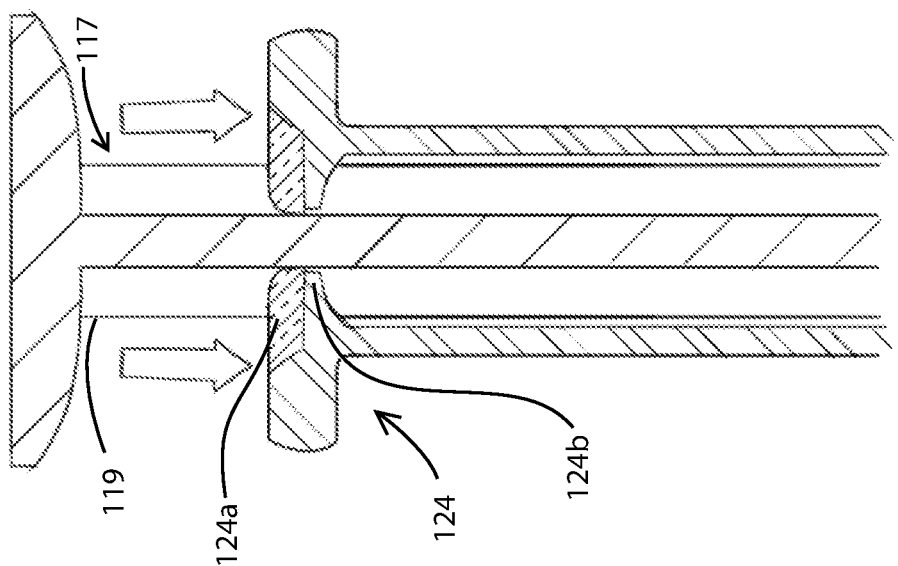

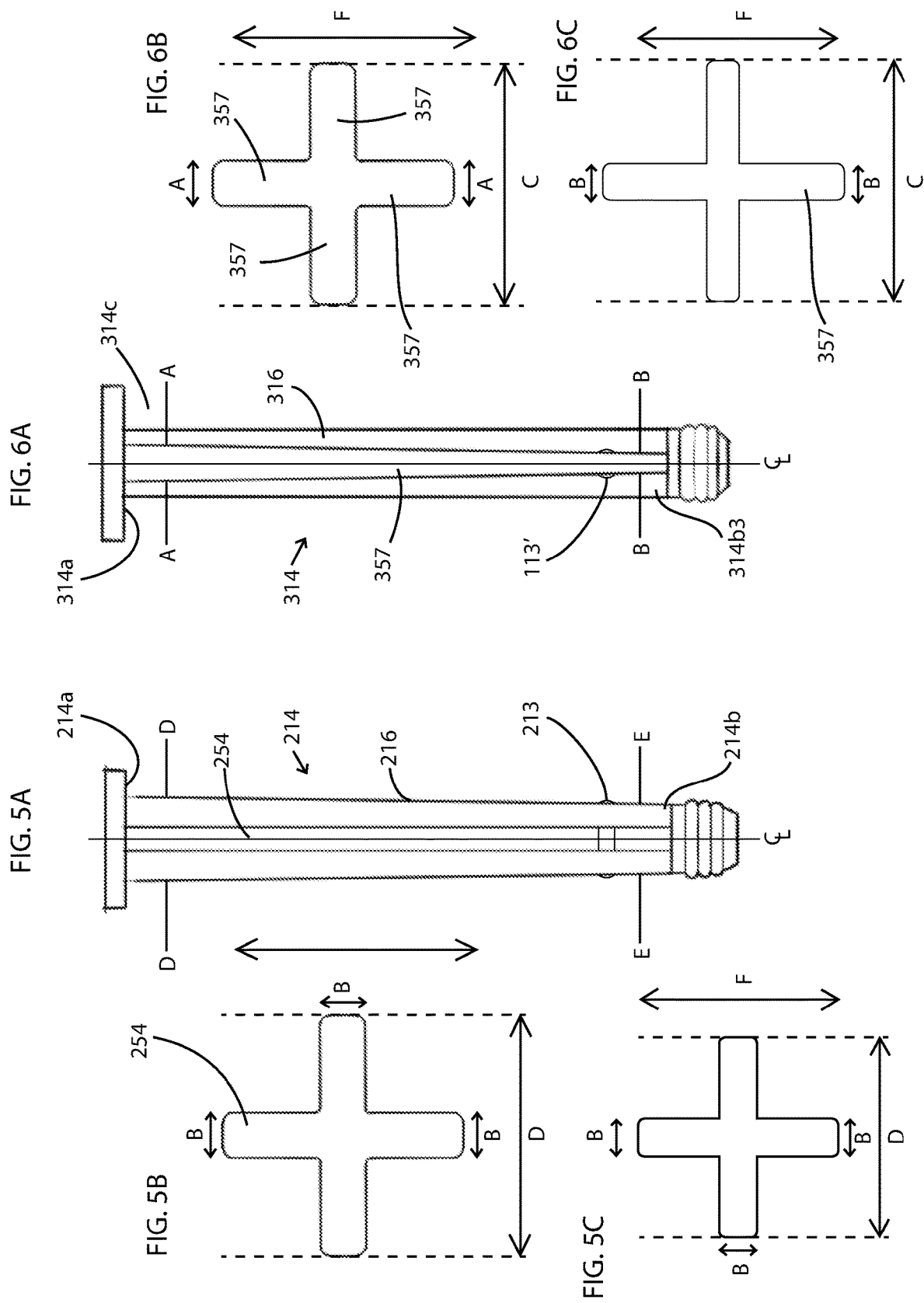

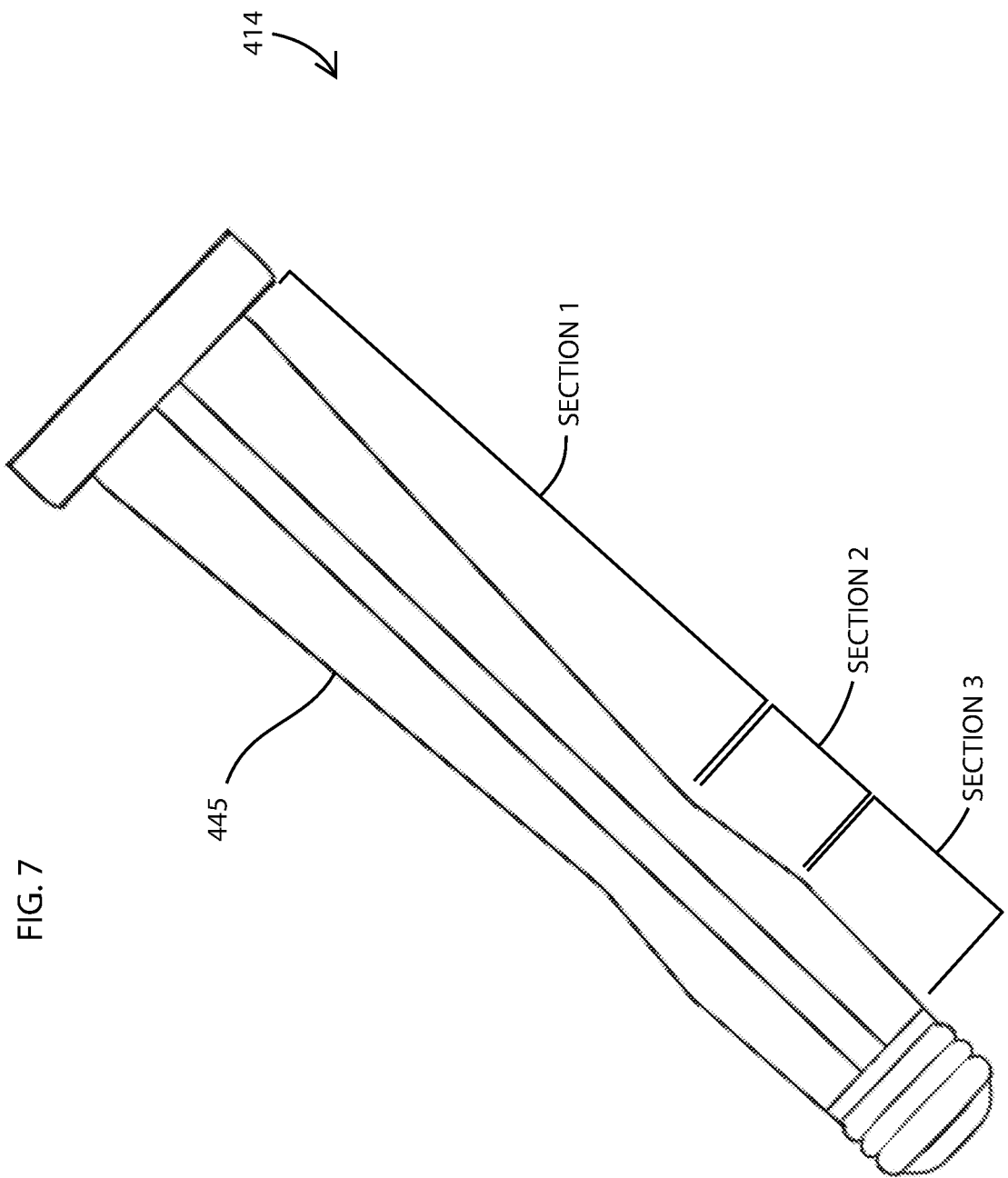

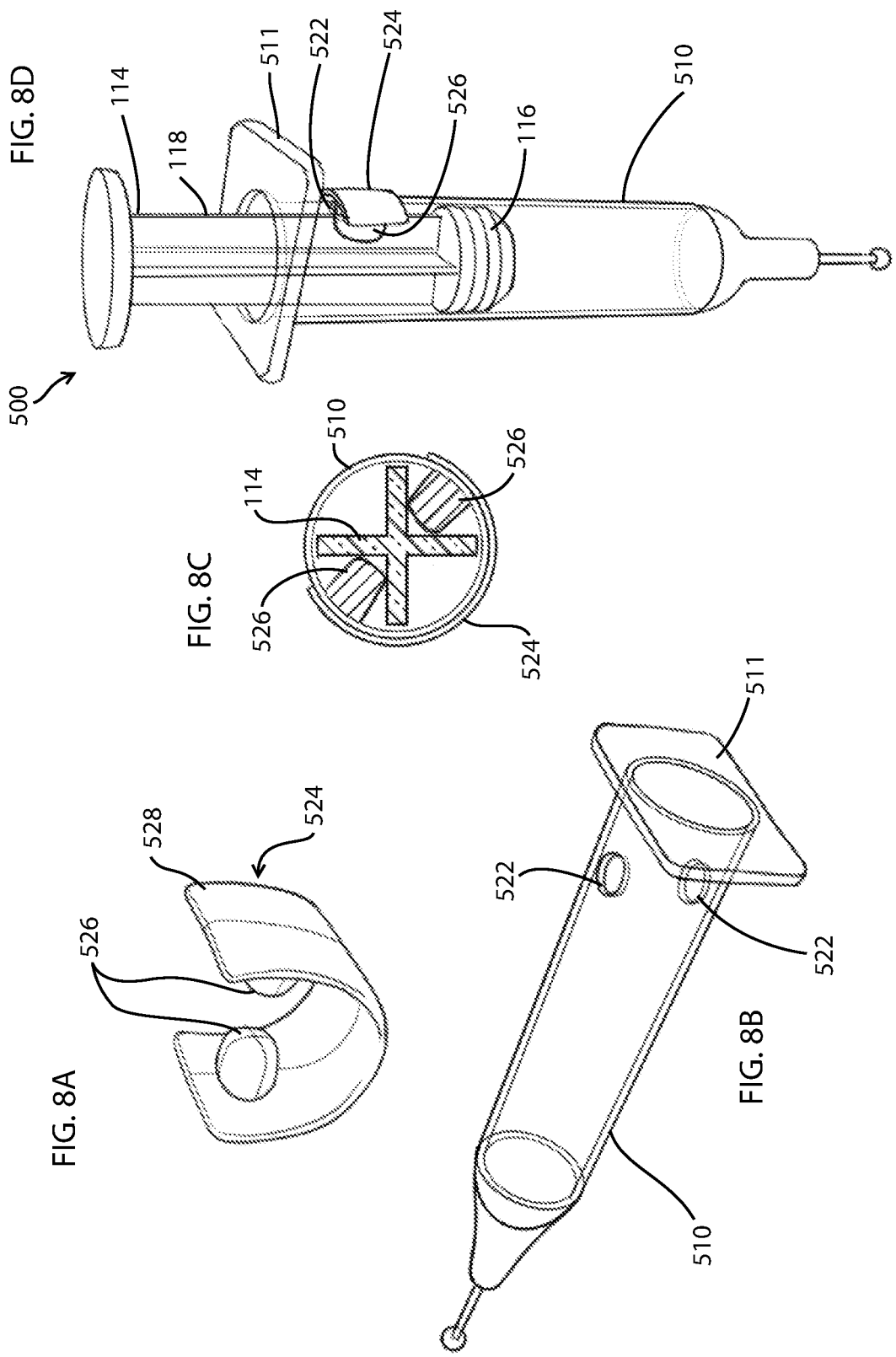

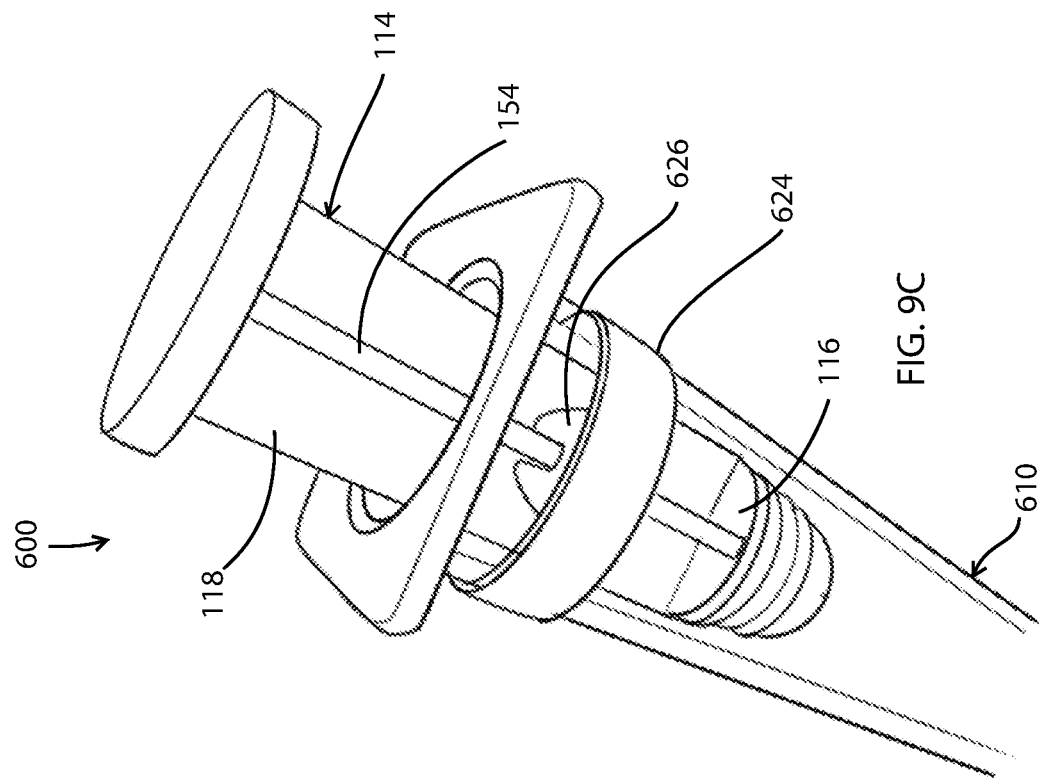
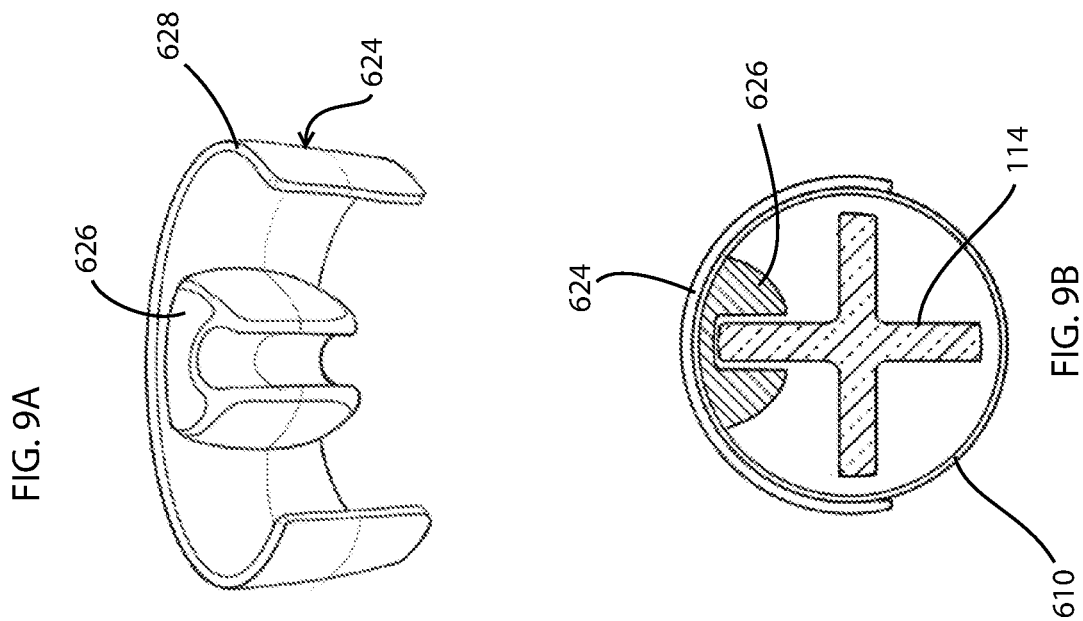
FIG. 9A  FIG. 9B  FIG. 9C

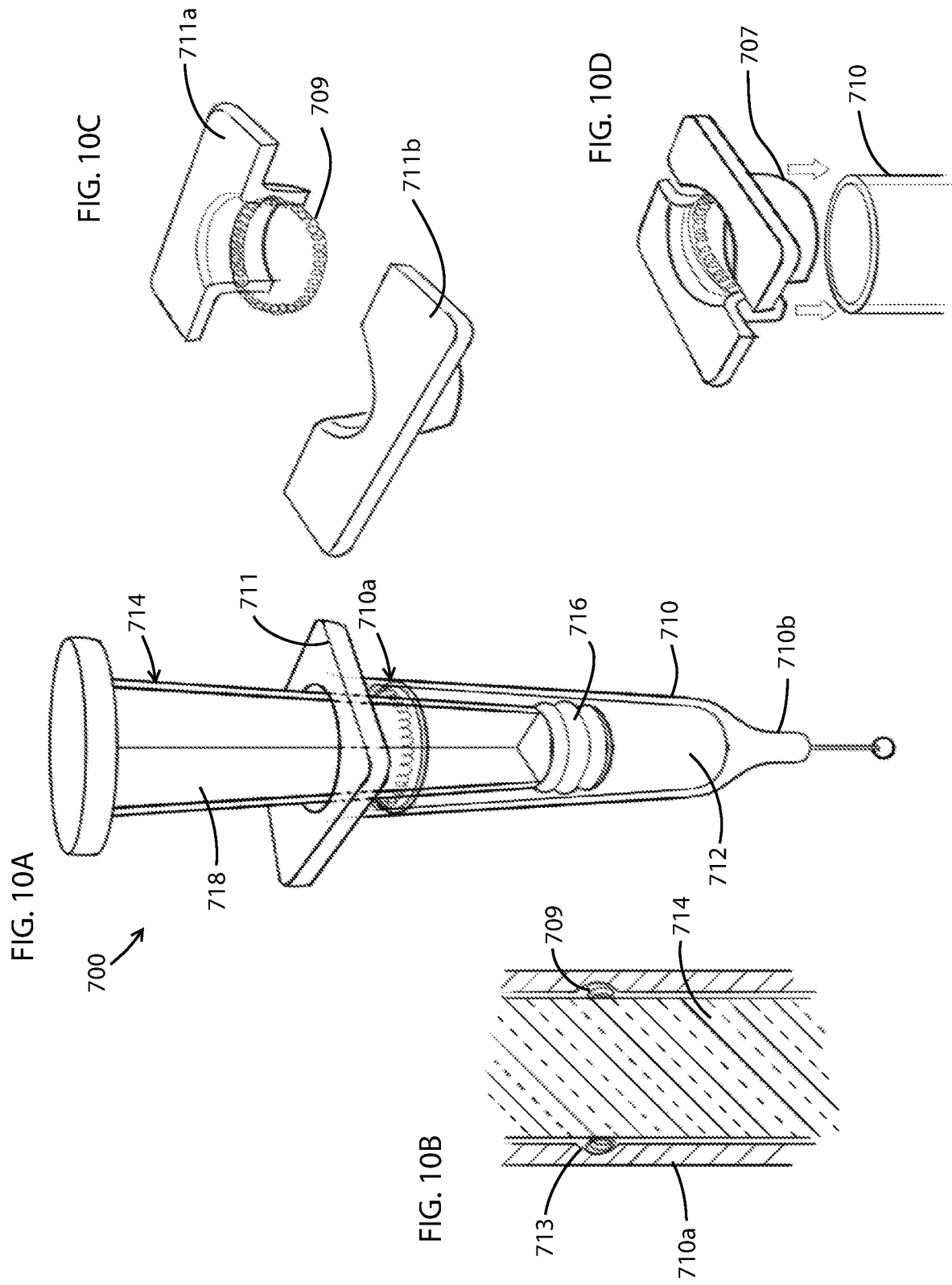

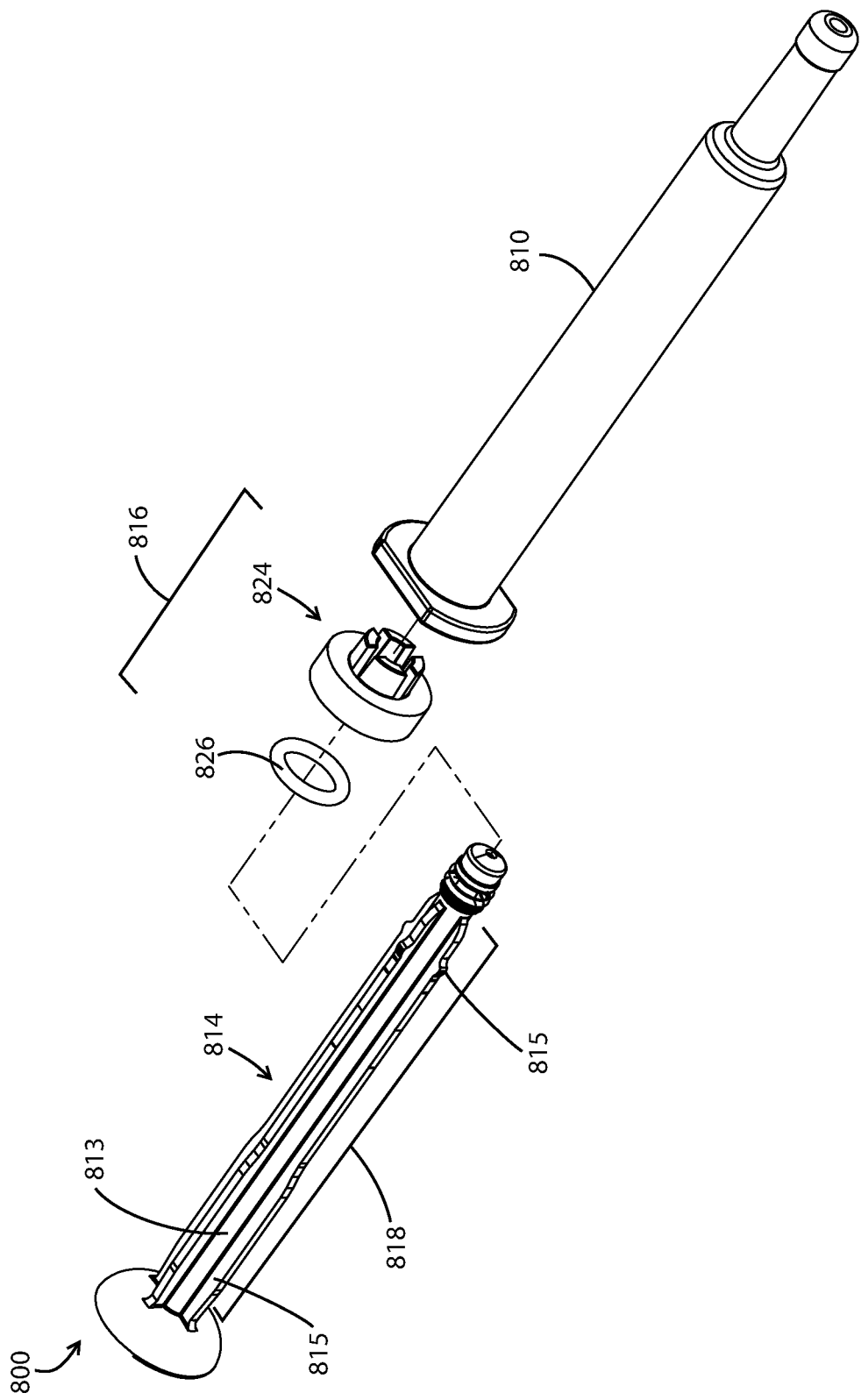

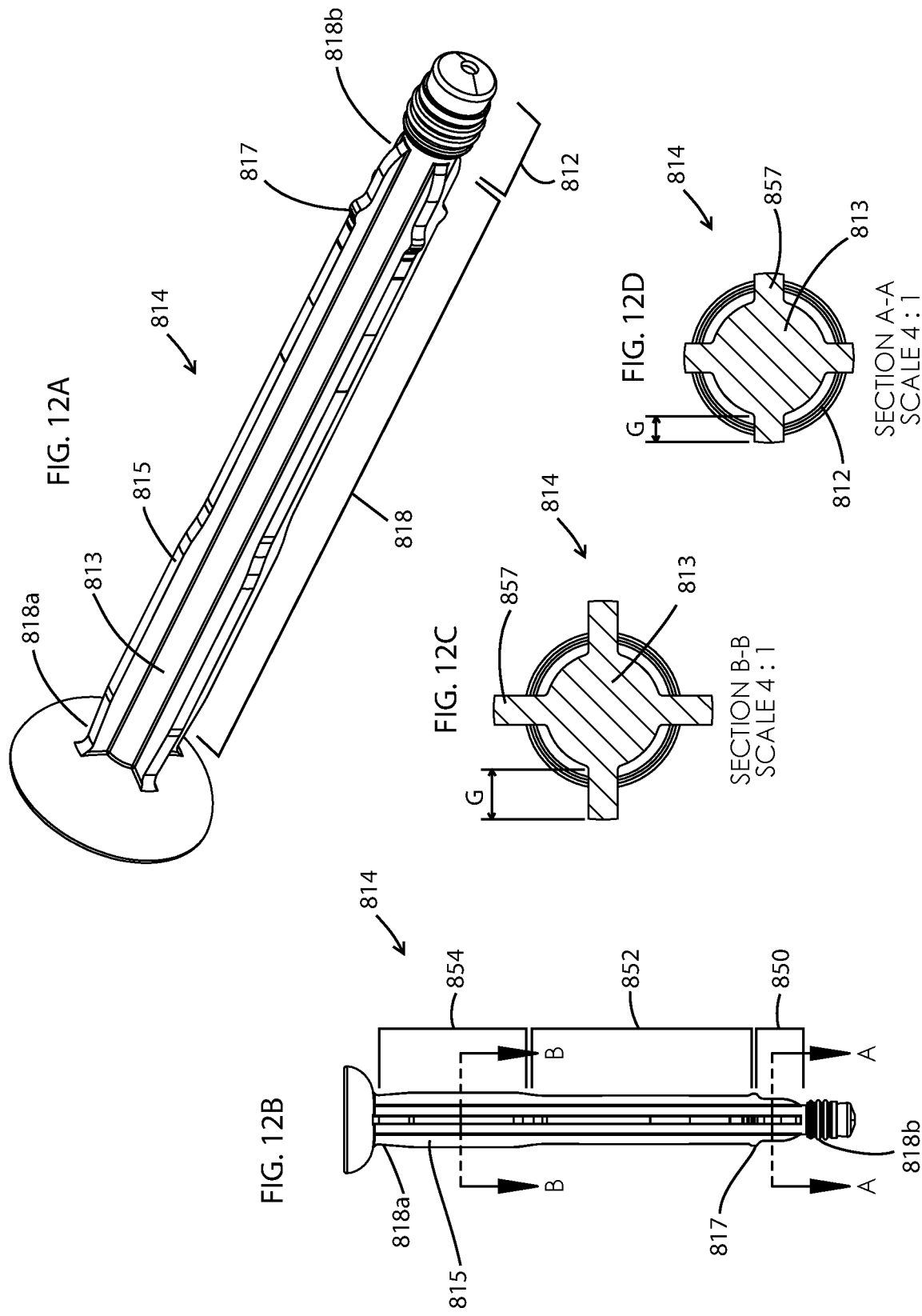

SECTION L-L
SCALE 4:1

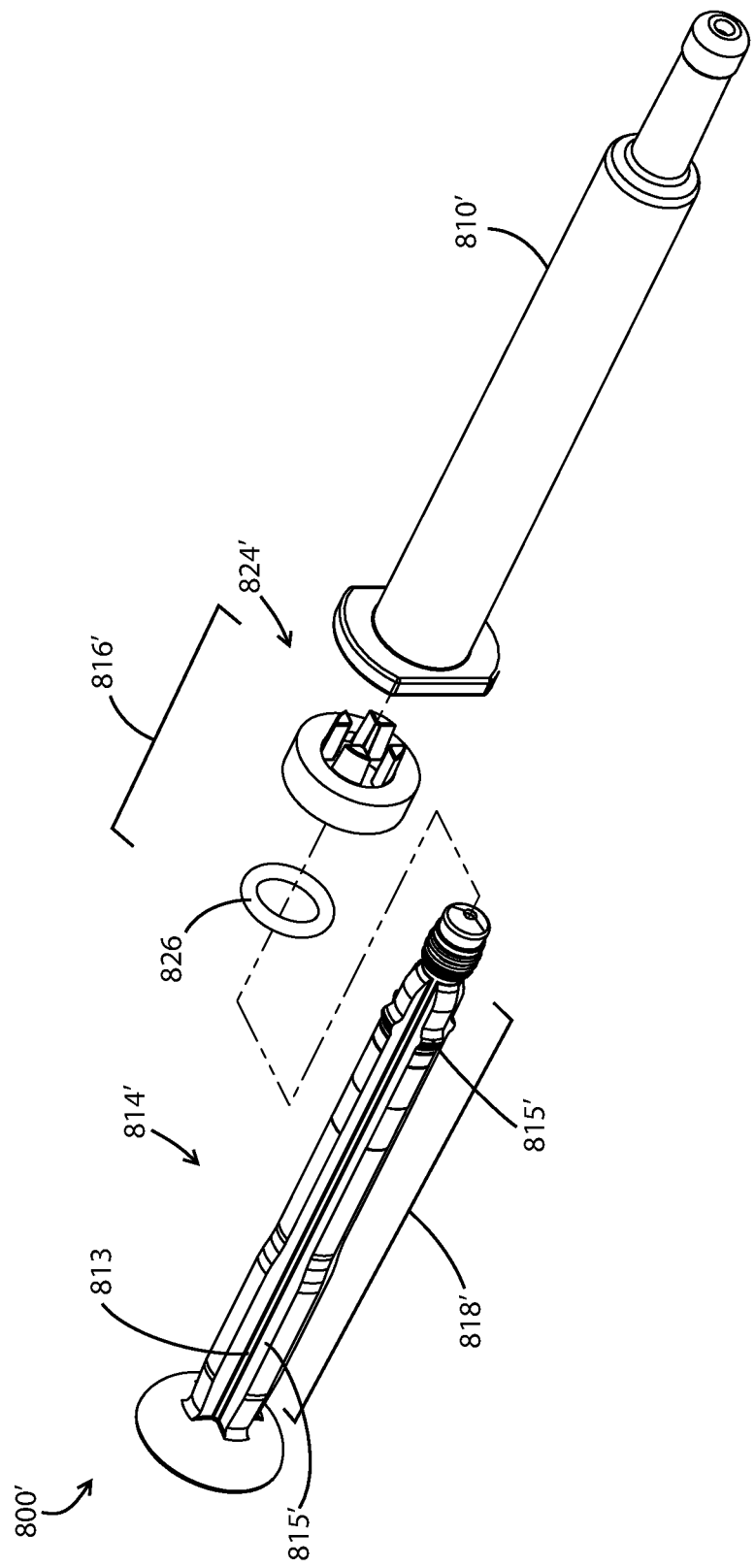

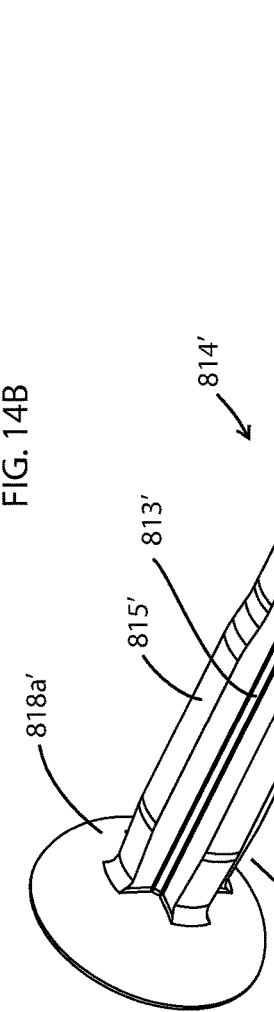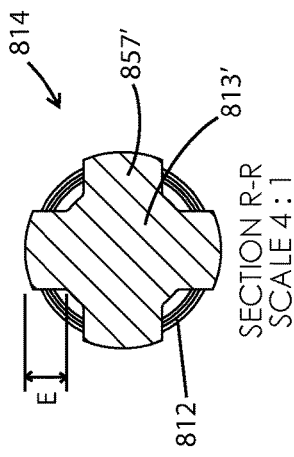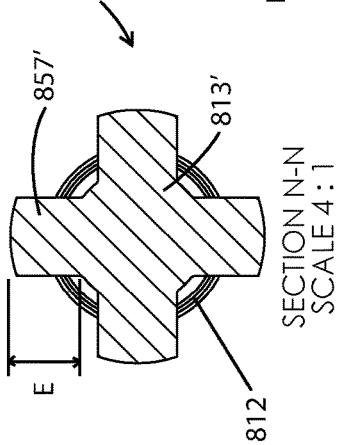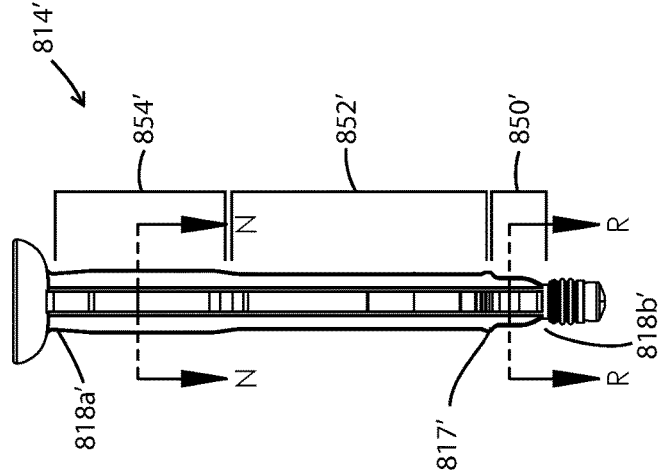

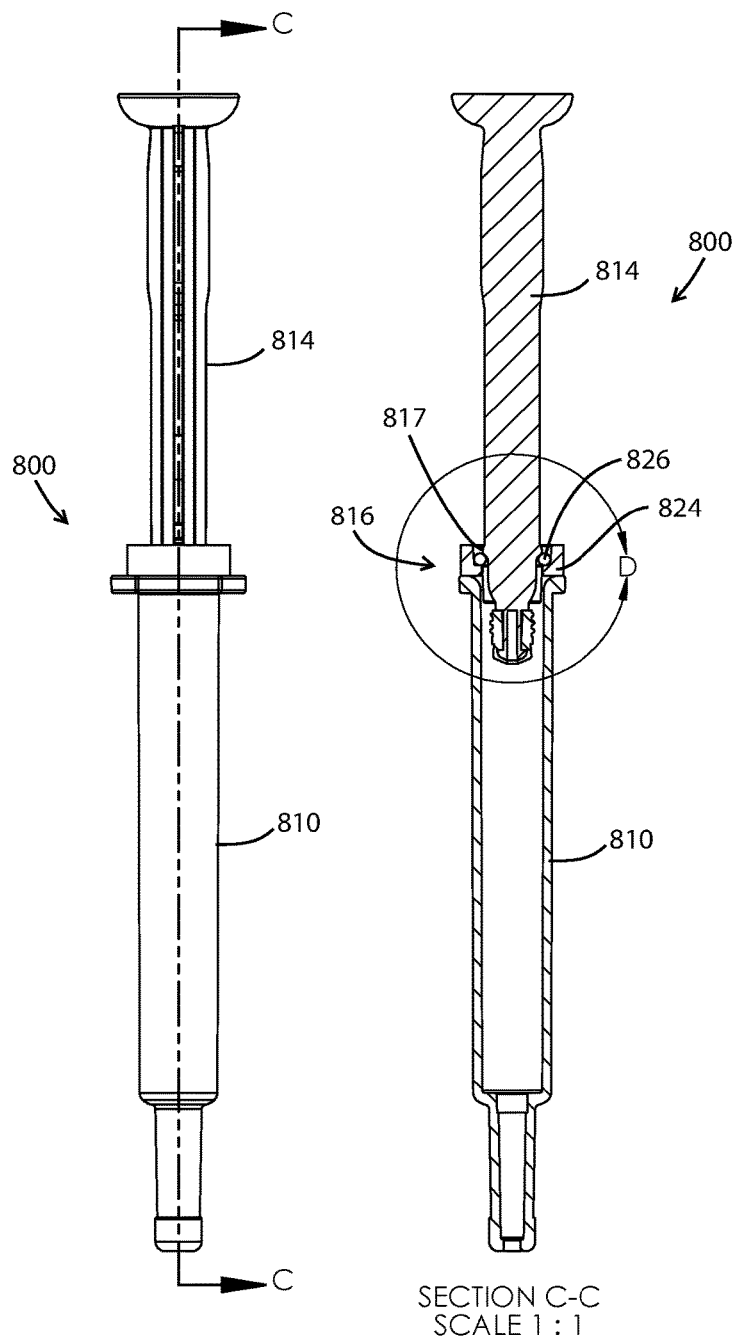

FIG. 17A
FIG. 17B
FIG. 17C
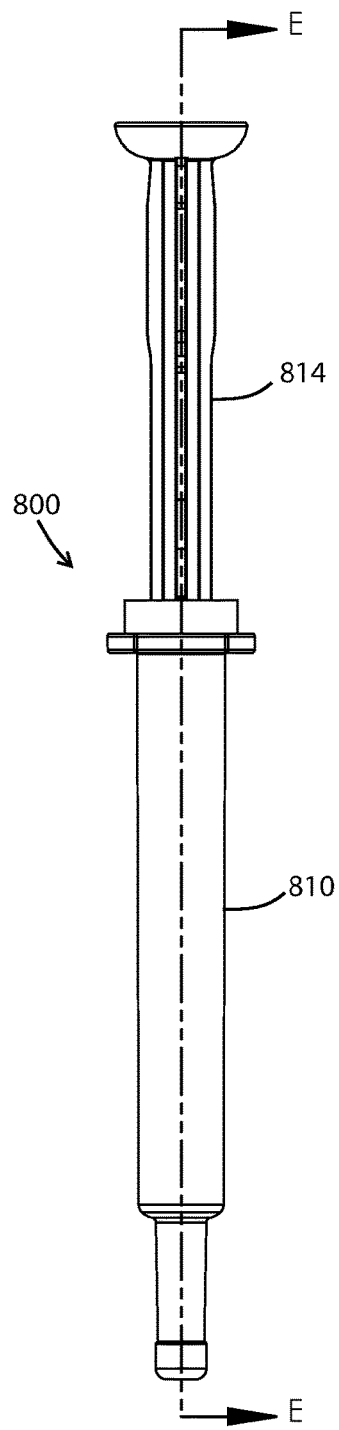
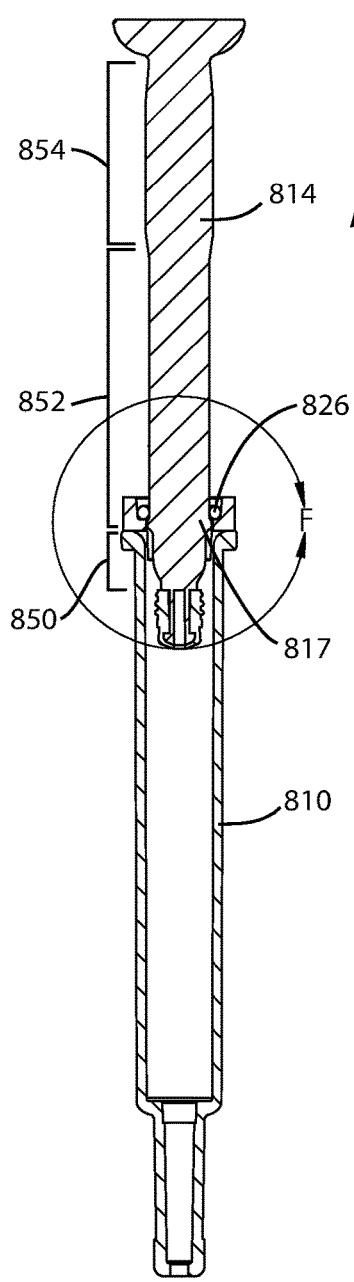
SECTION E-E
SCALE 1 : 1
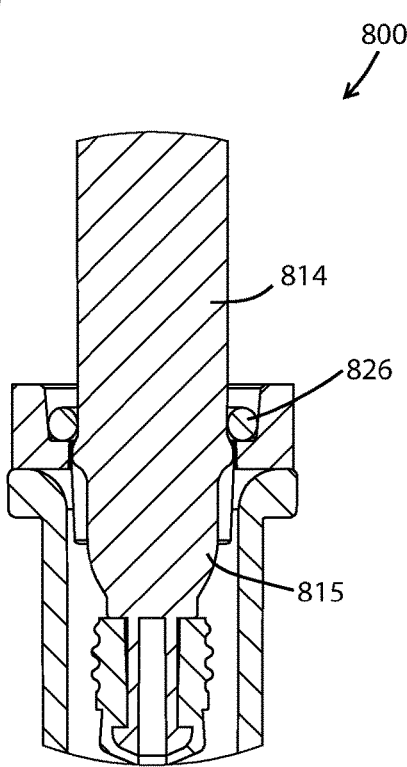
DETAIL F
SCALE 2 : 1

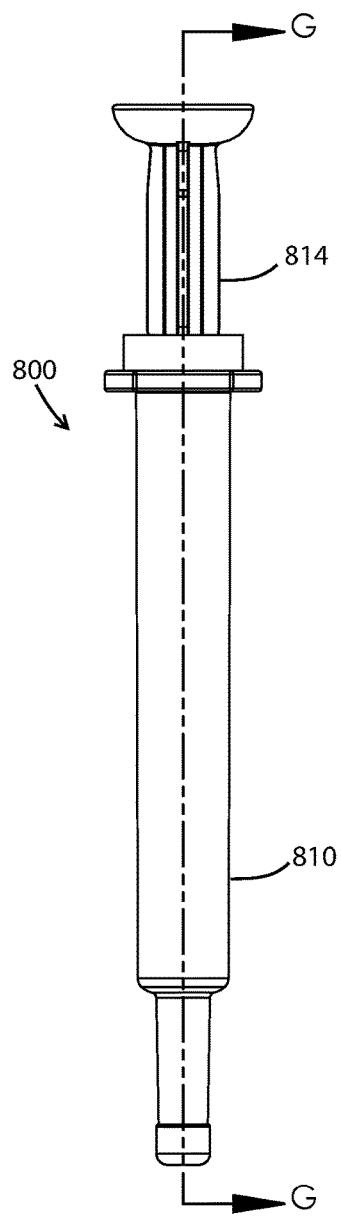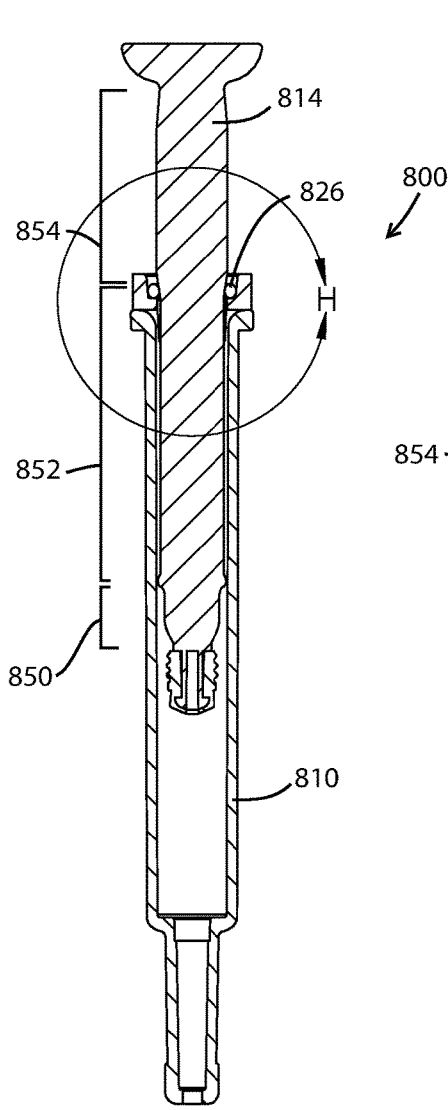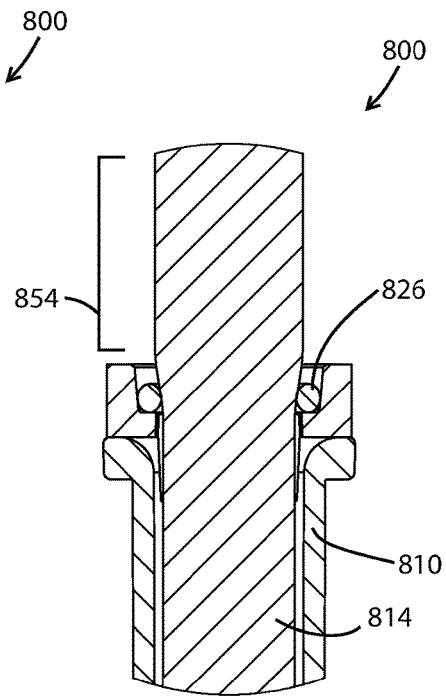
FIG. 18A
FIG. 18B
FIG. 18C
SECTION G-G
SCALE 1 : 1
DETAIL H
SCALE 2 : 1

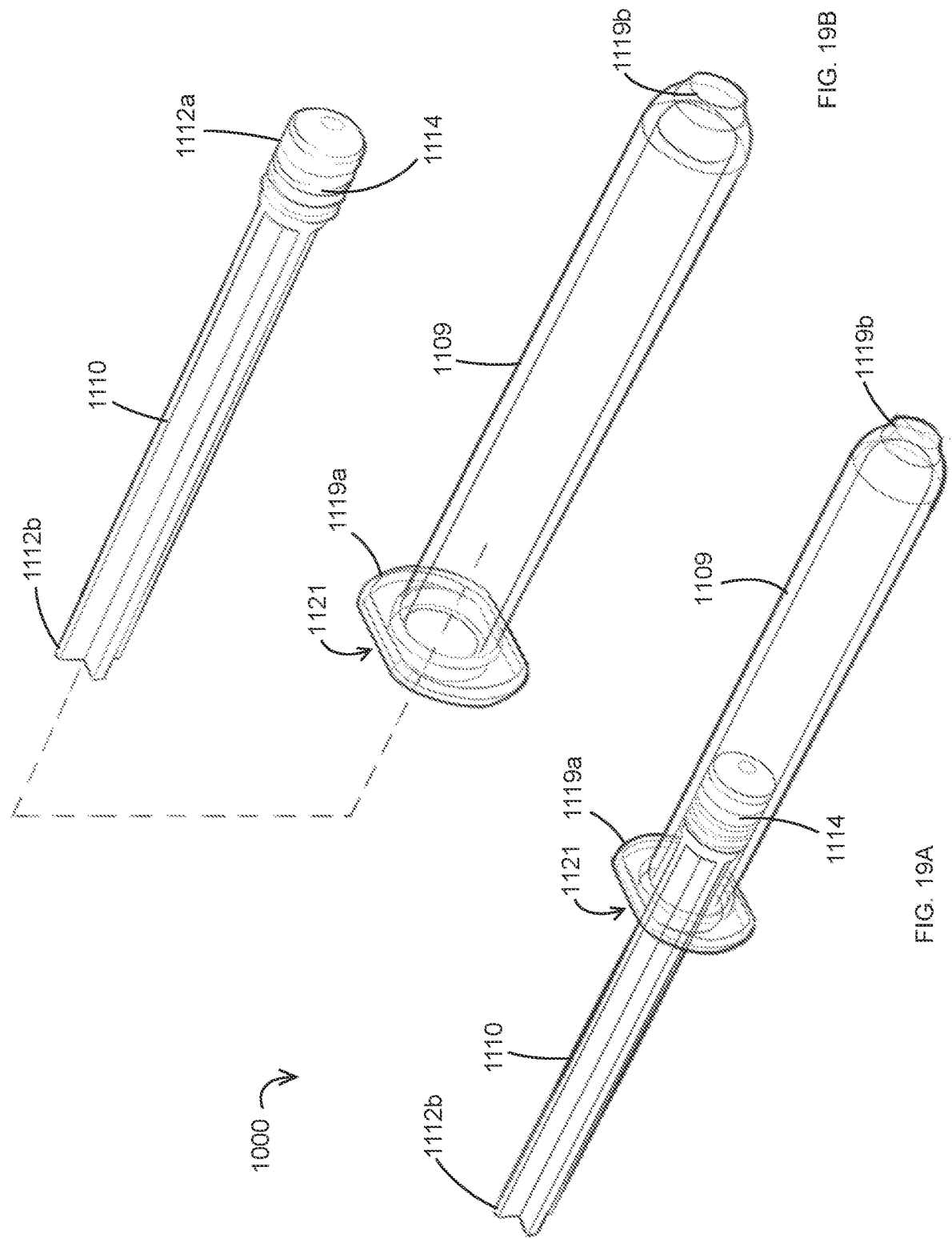

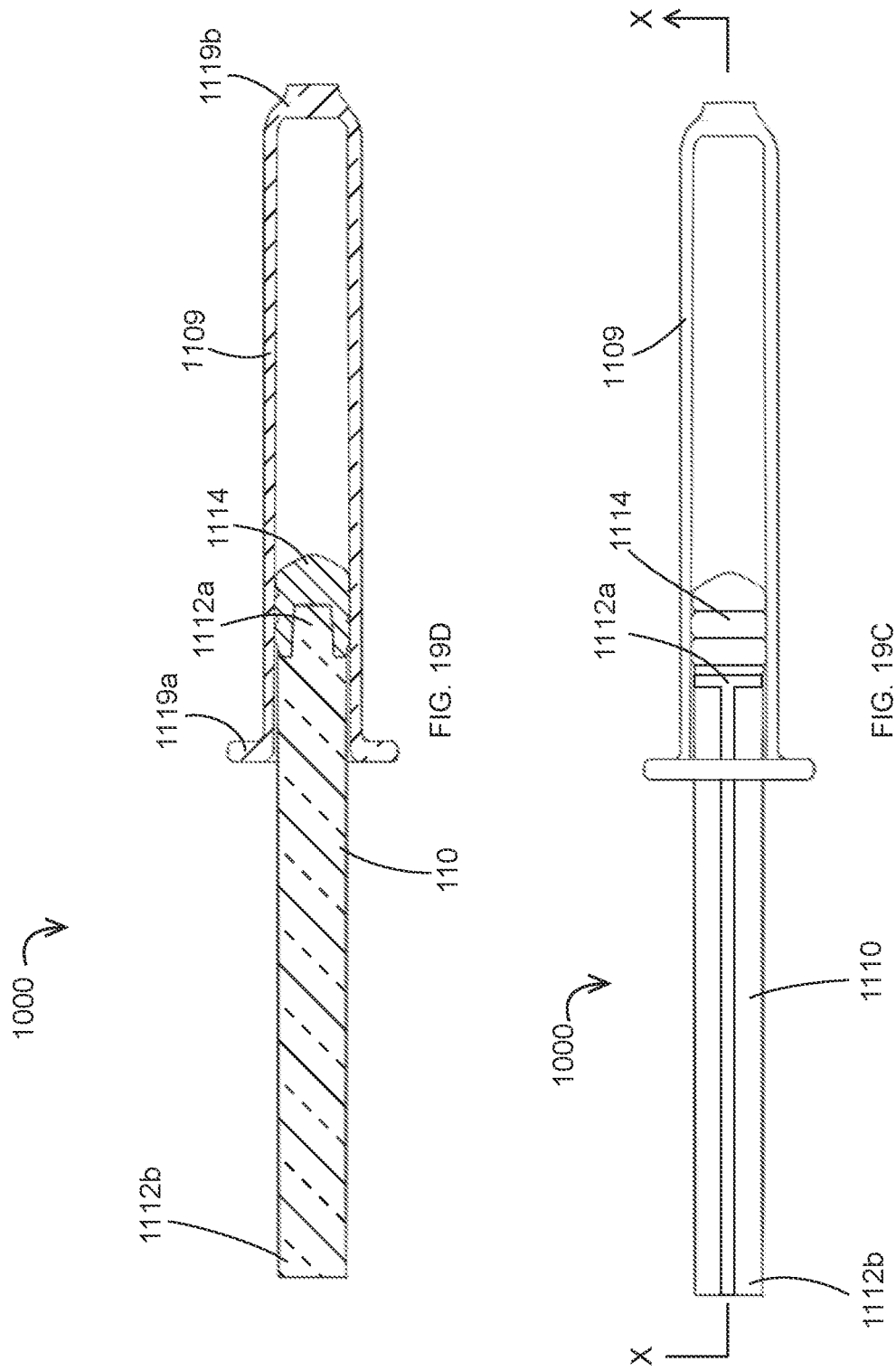

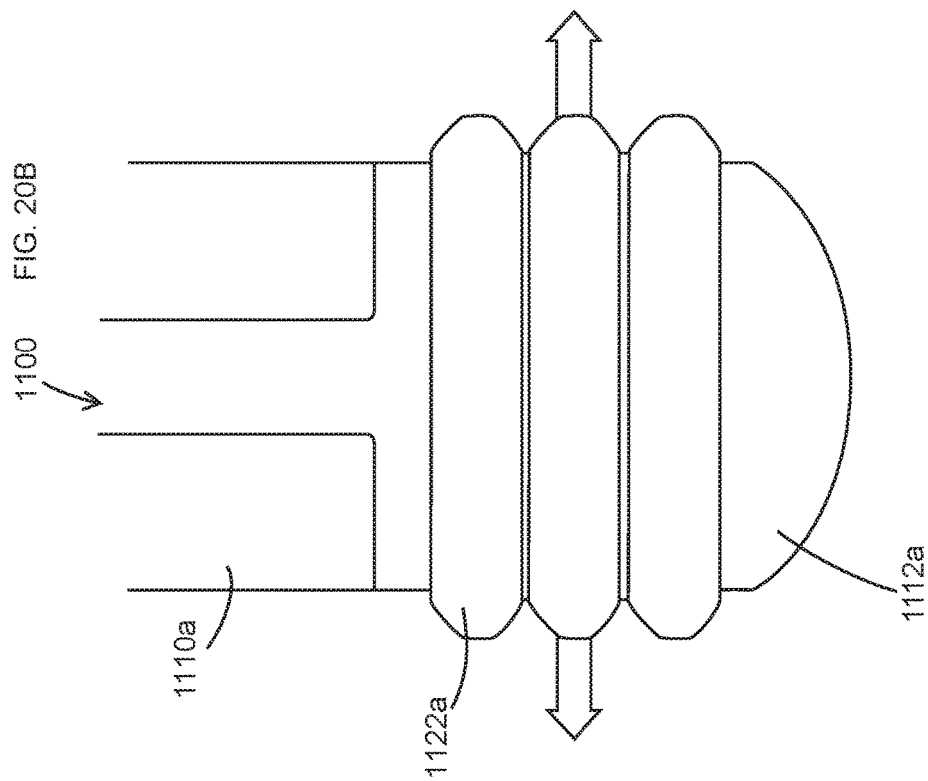
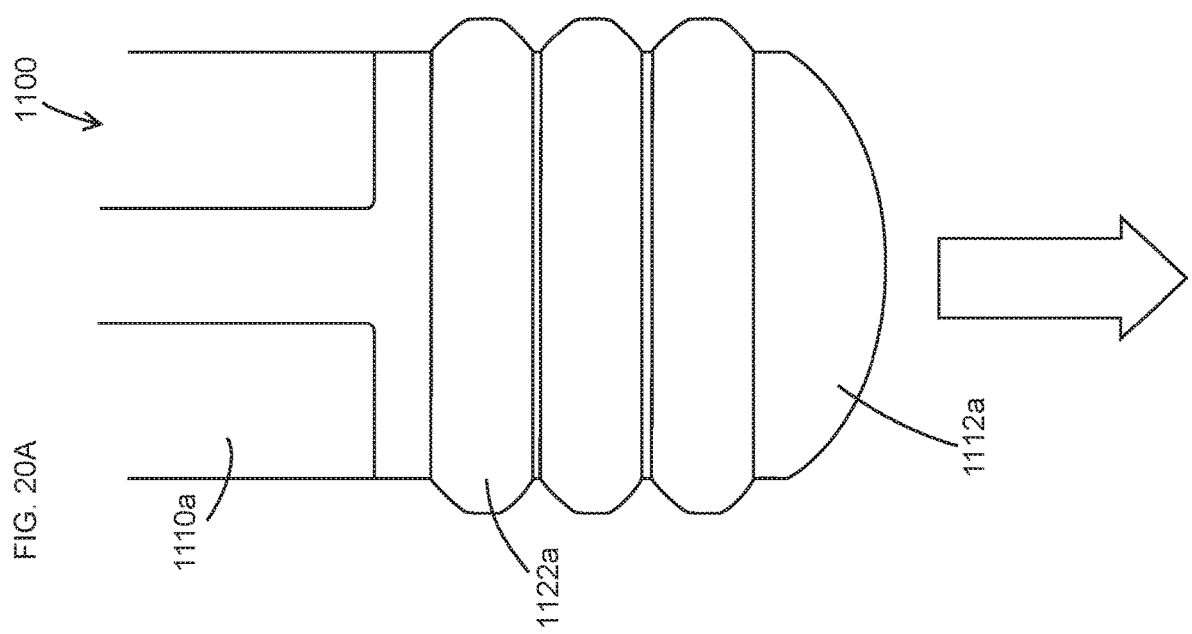

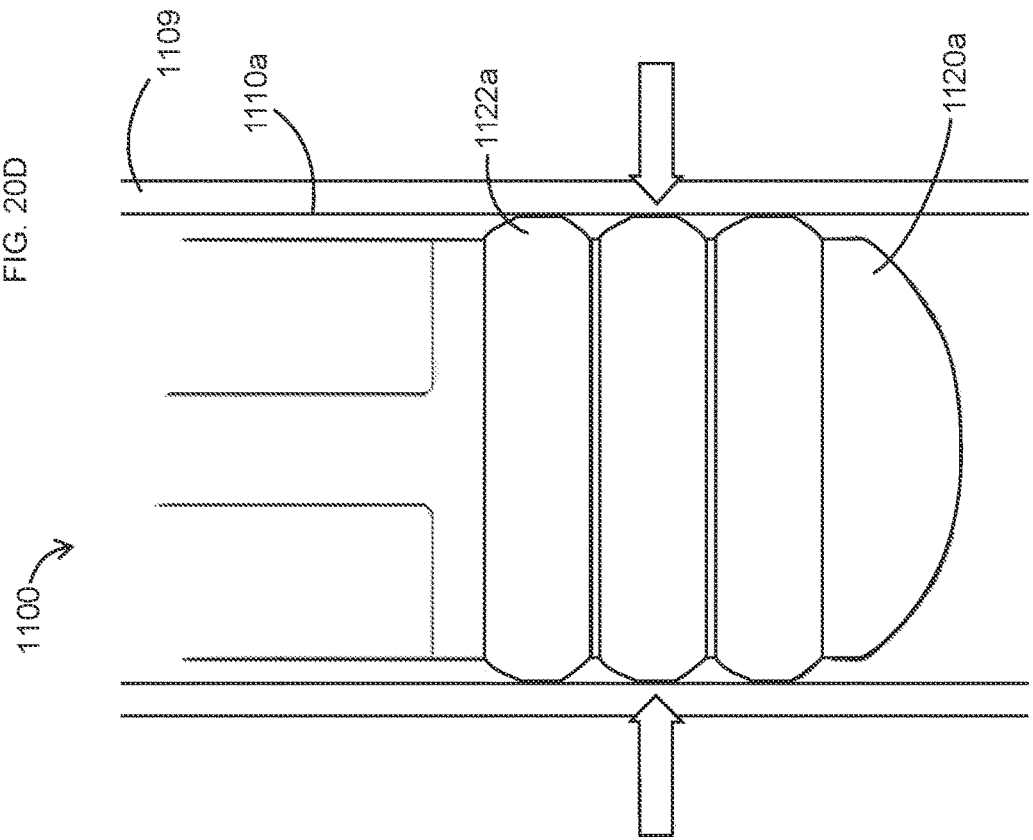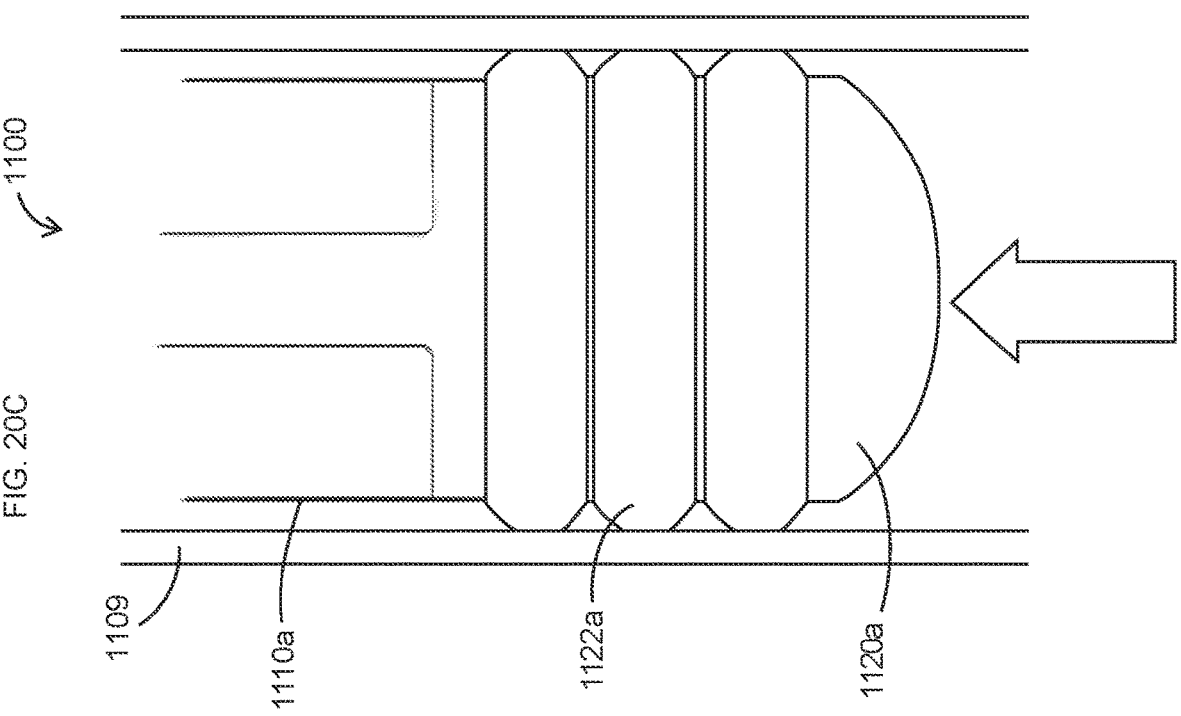

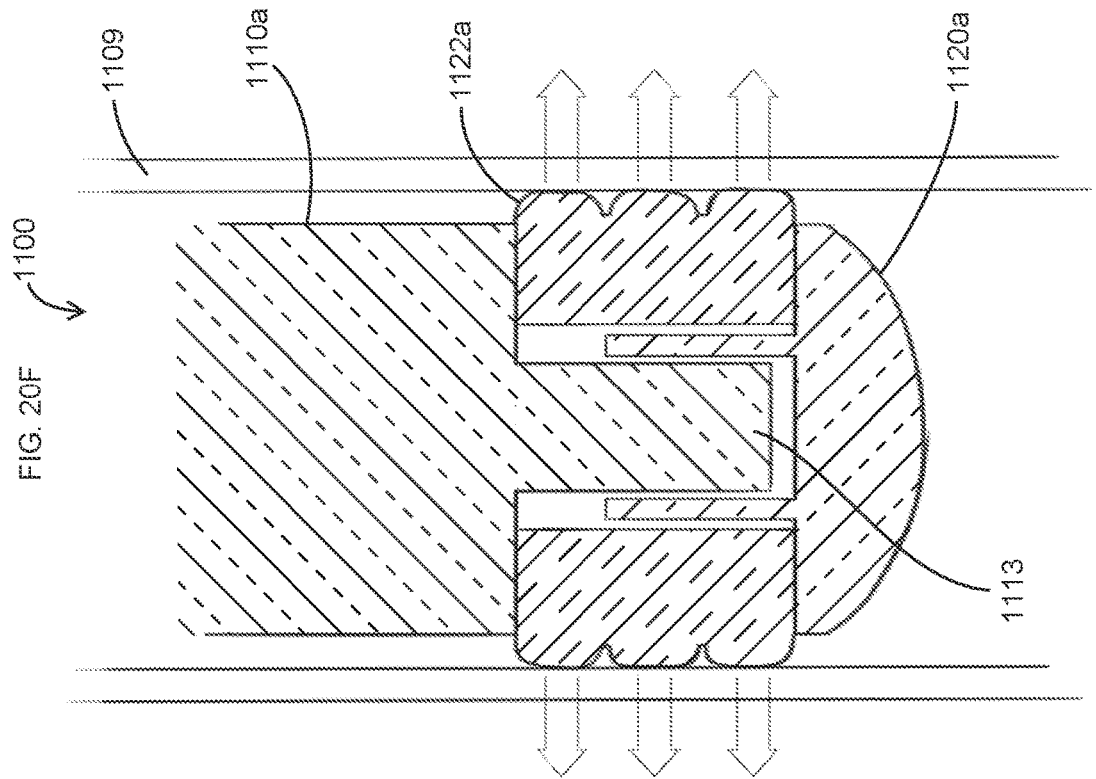
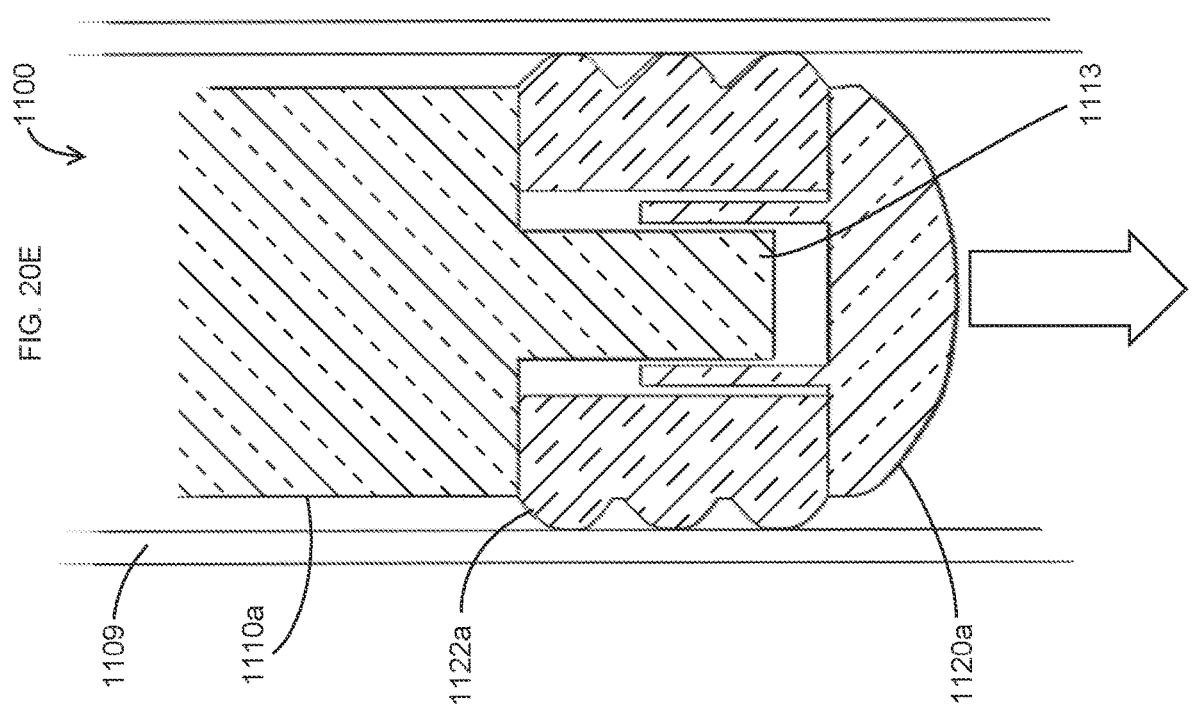

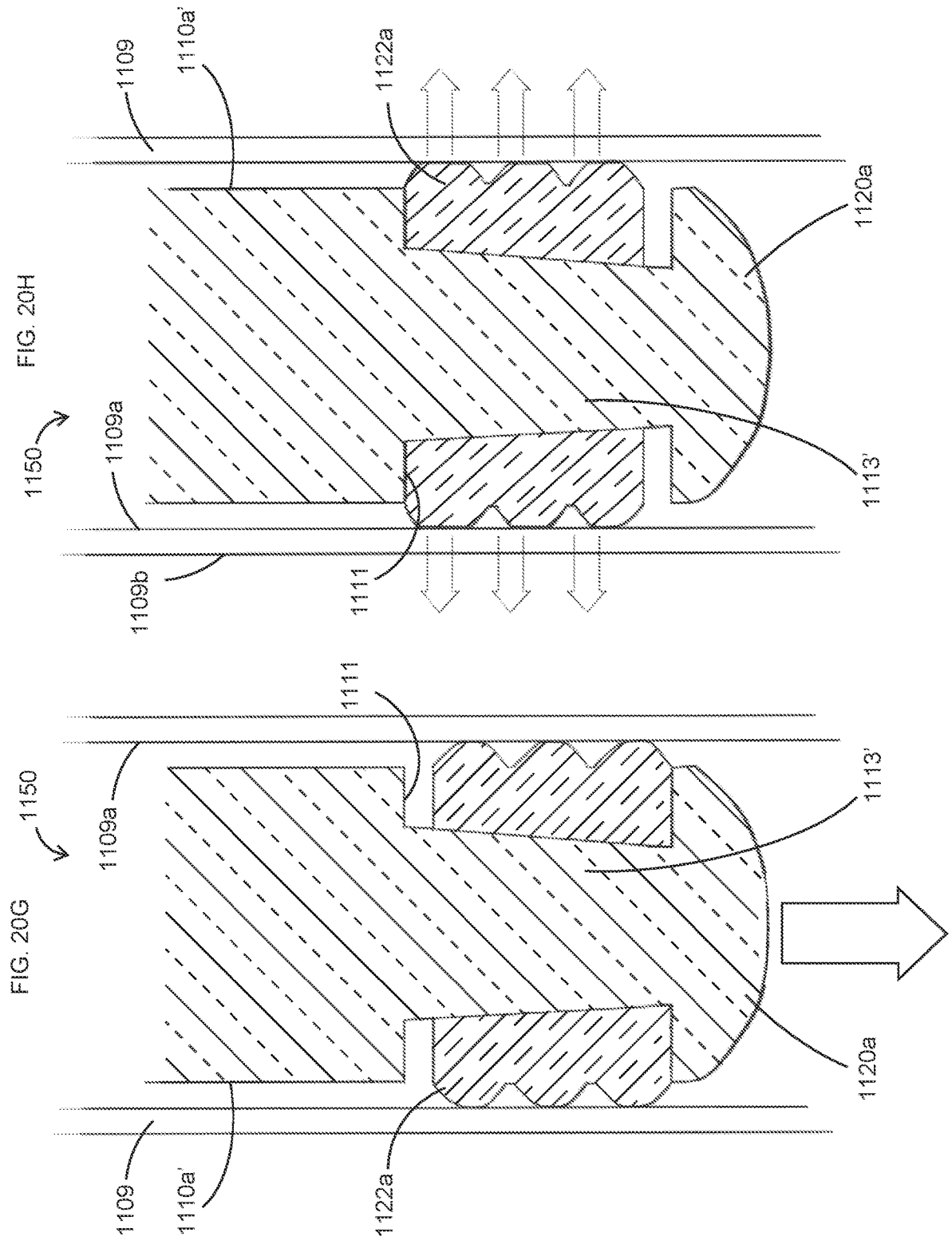

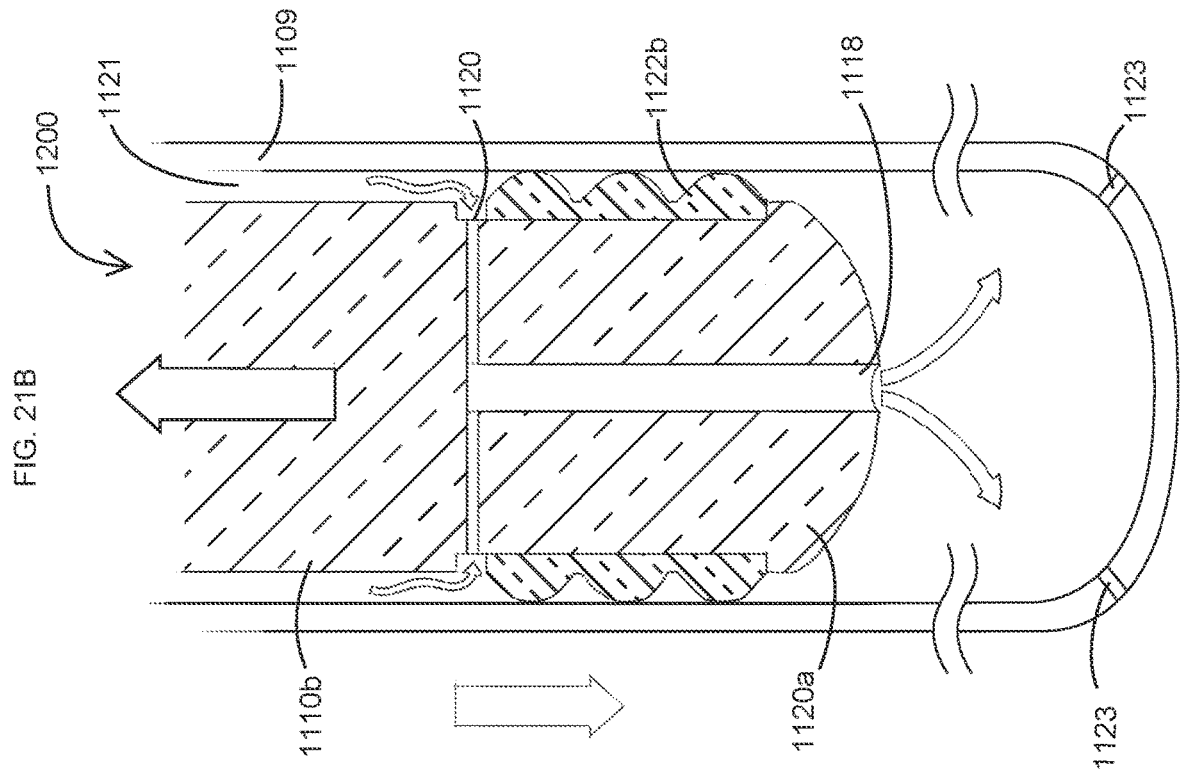
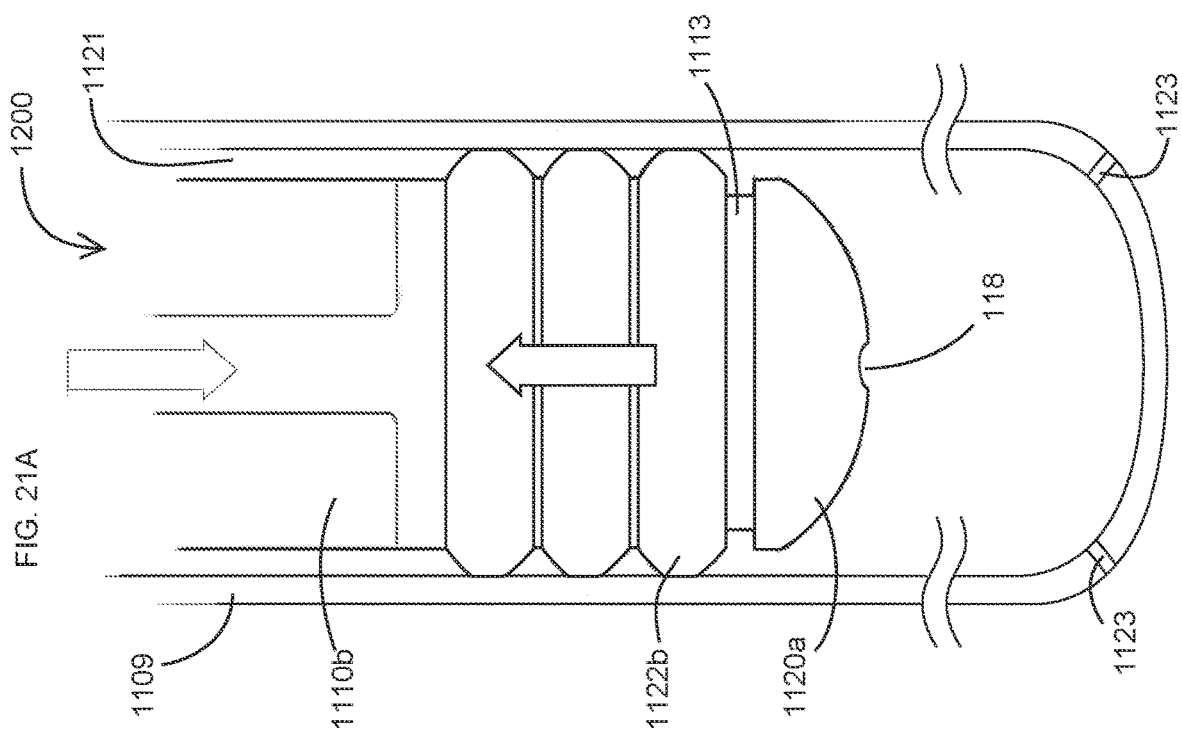

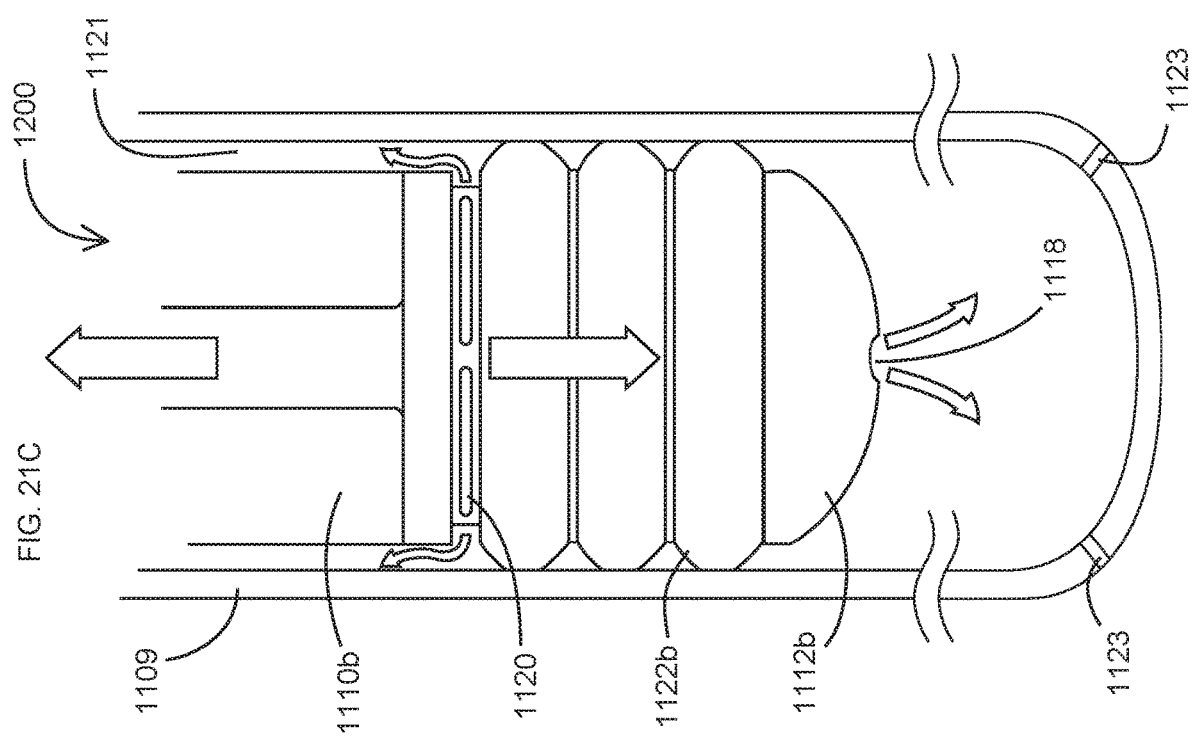

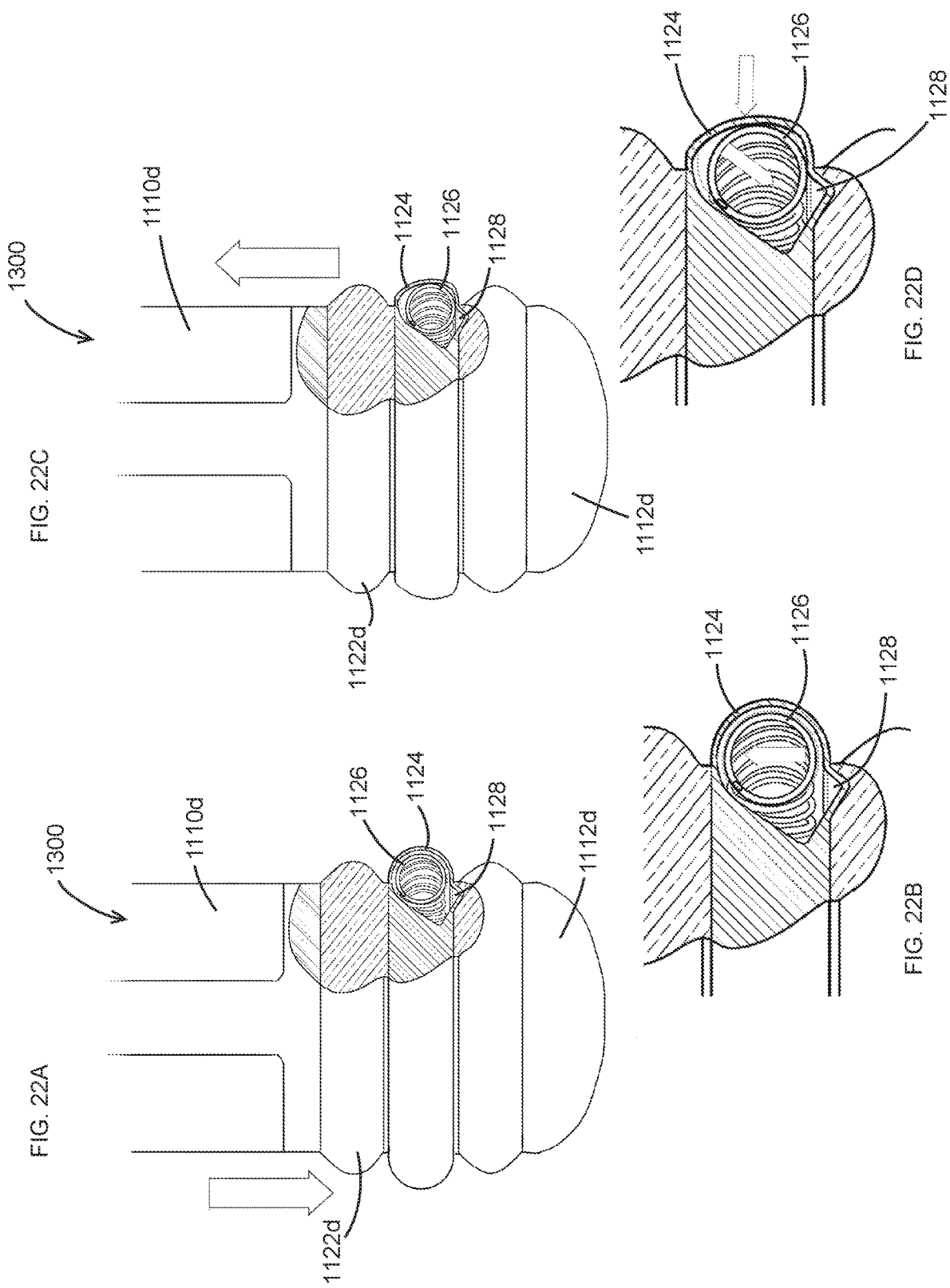

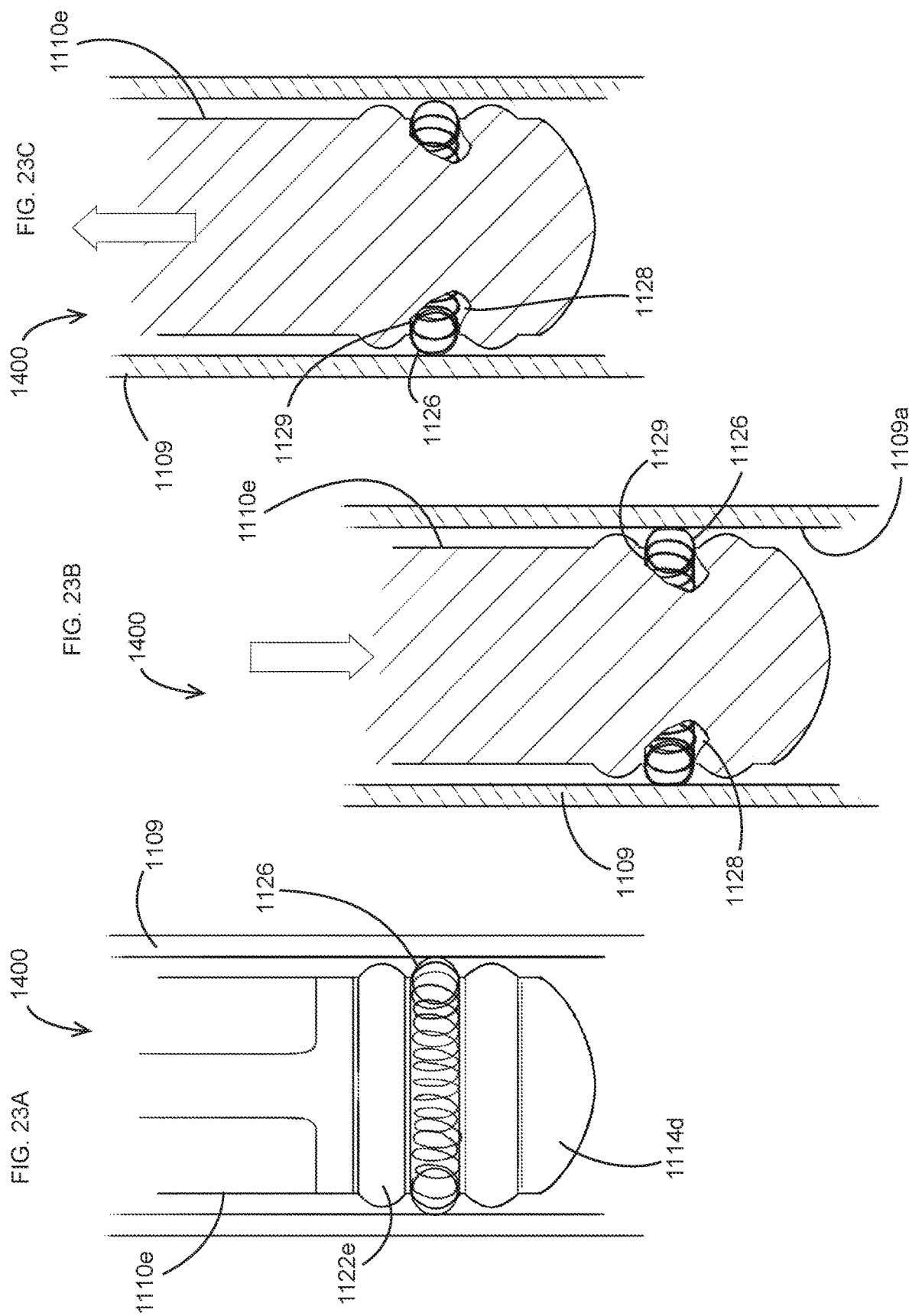

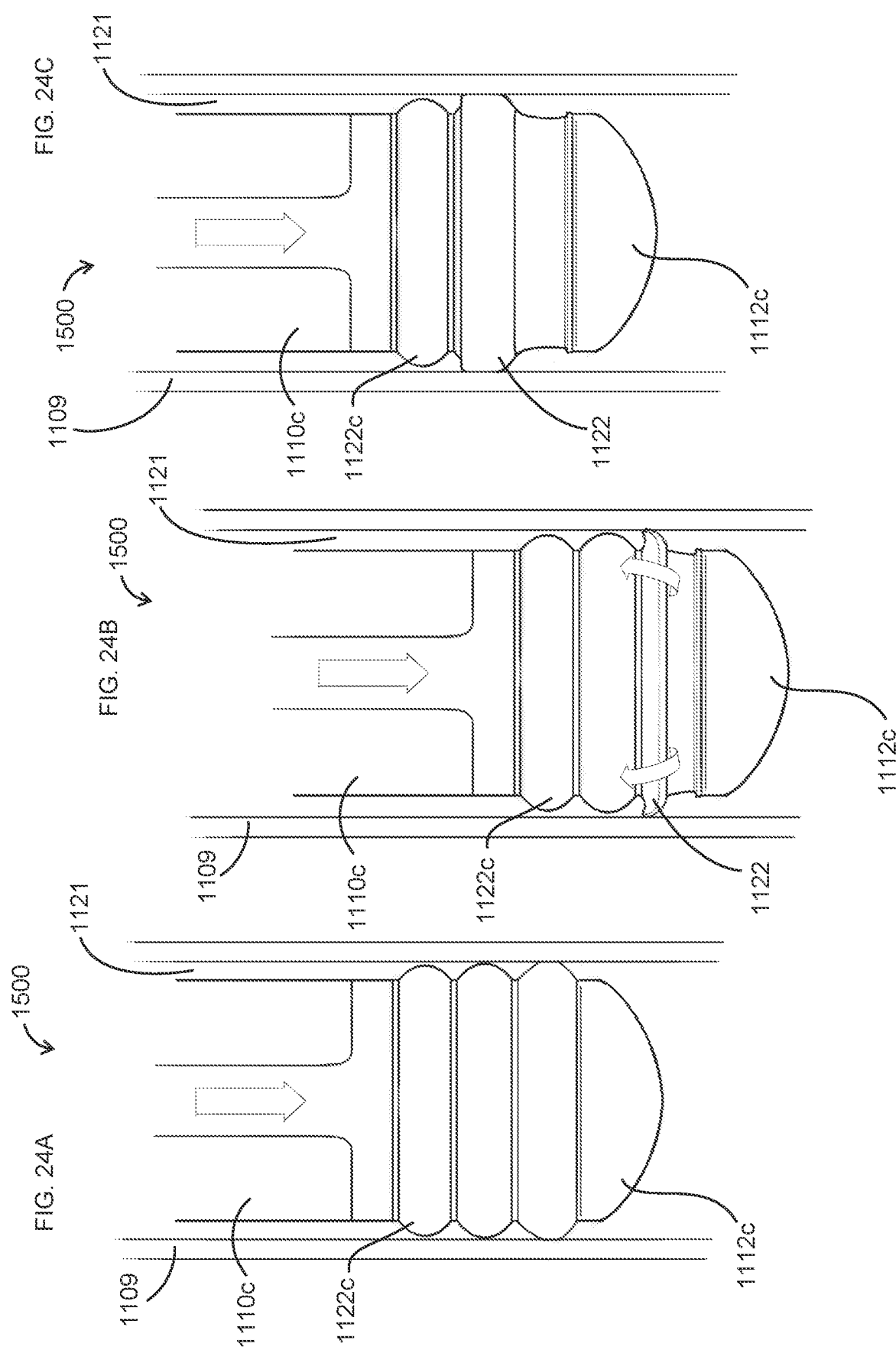

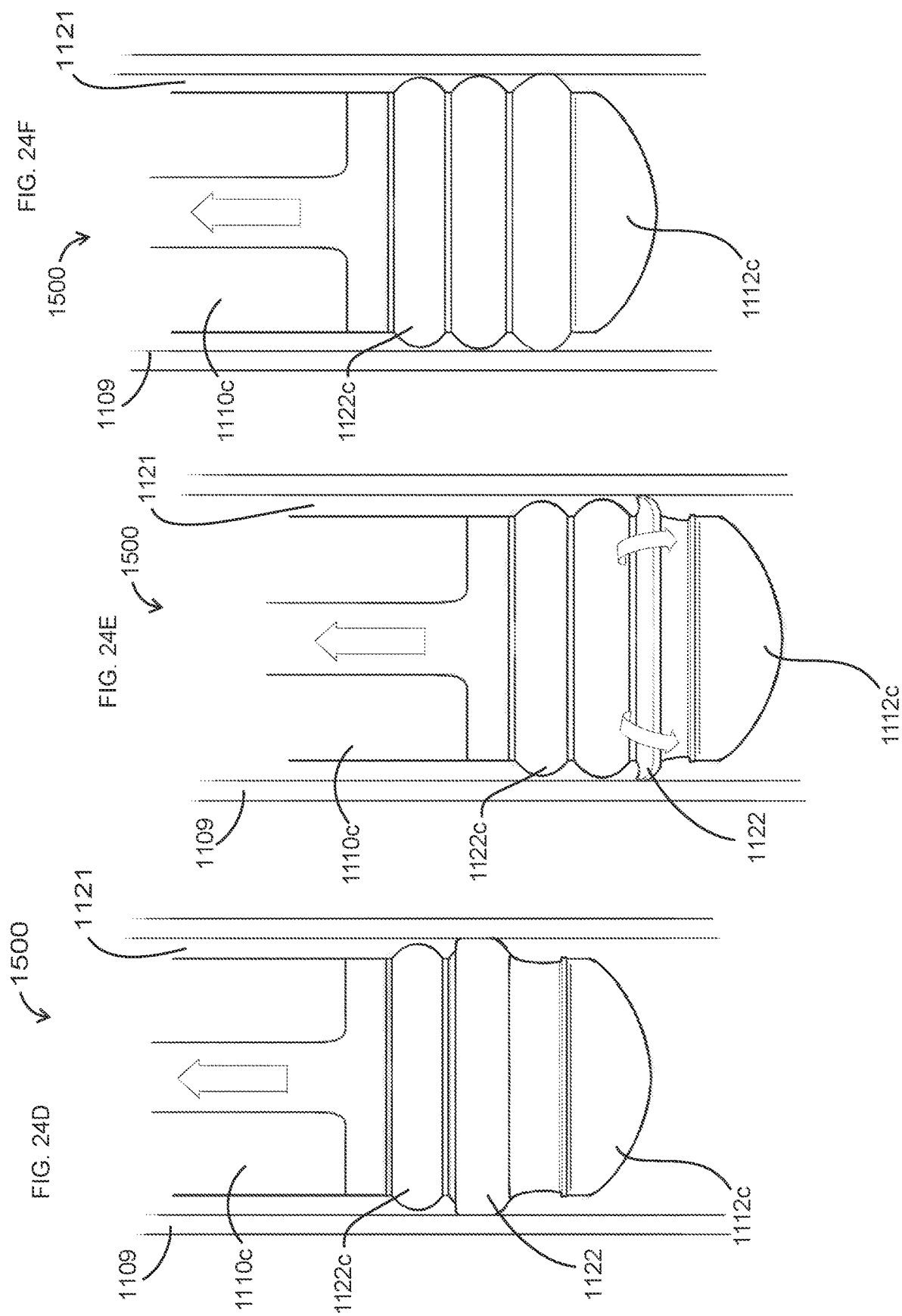

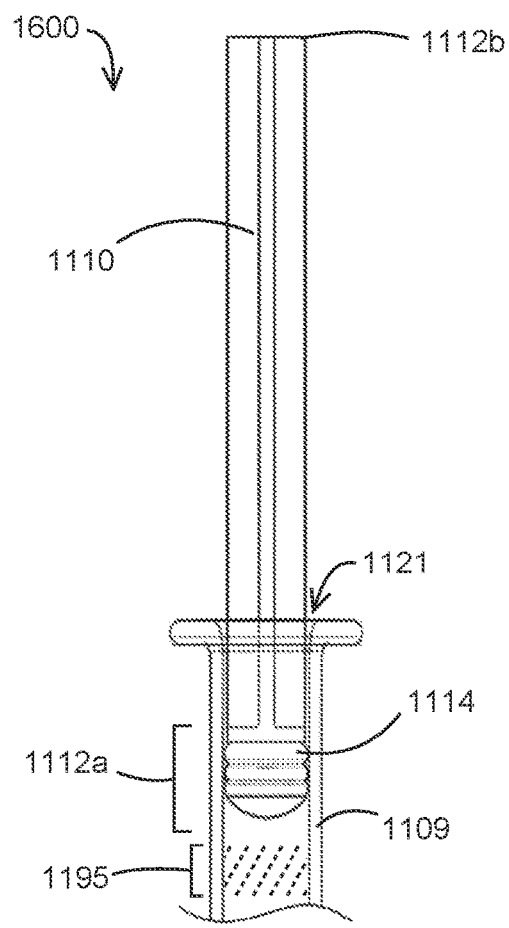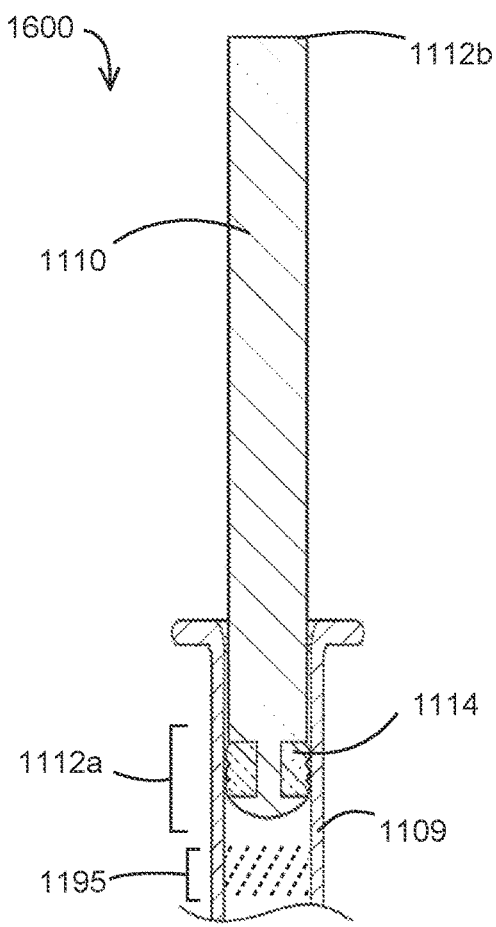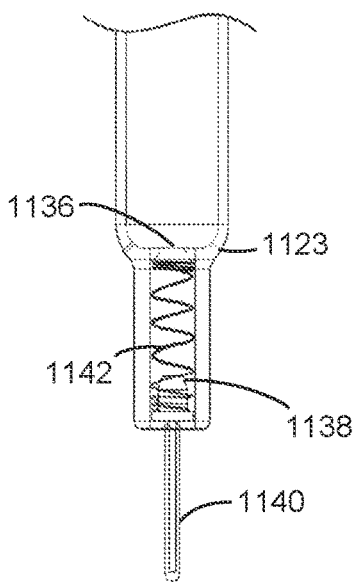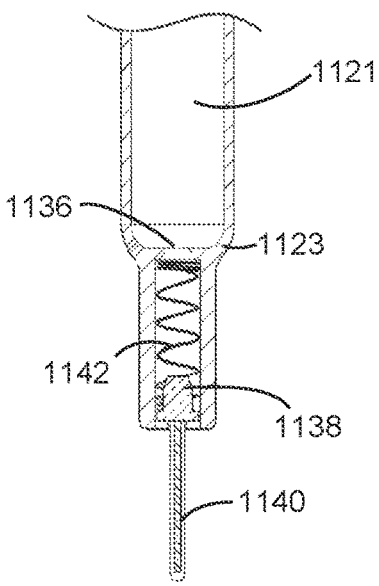
FIG. 25A
FIG. 25B

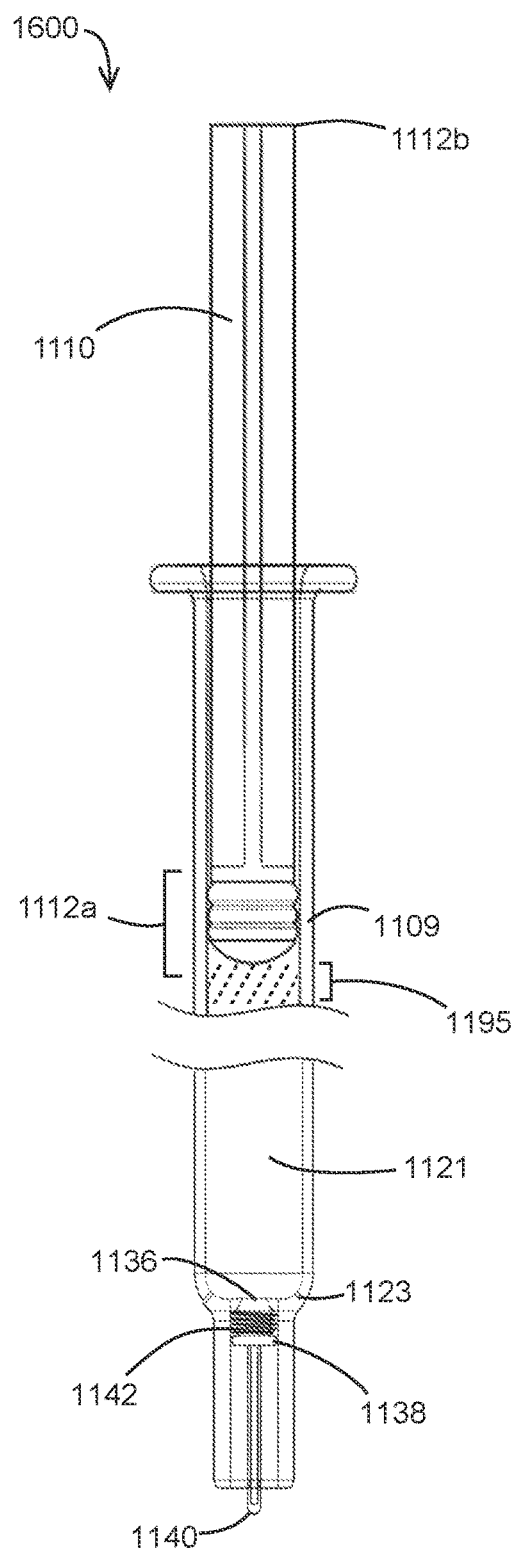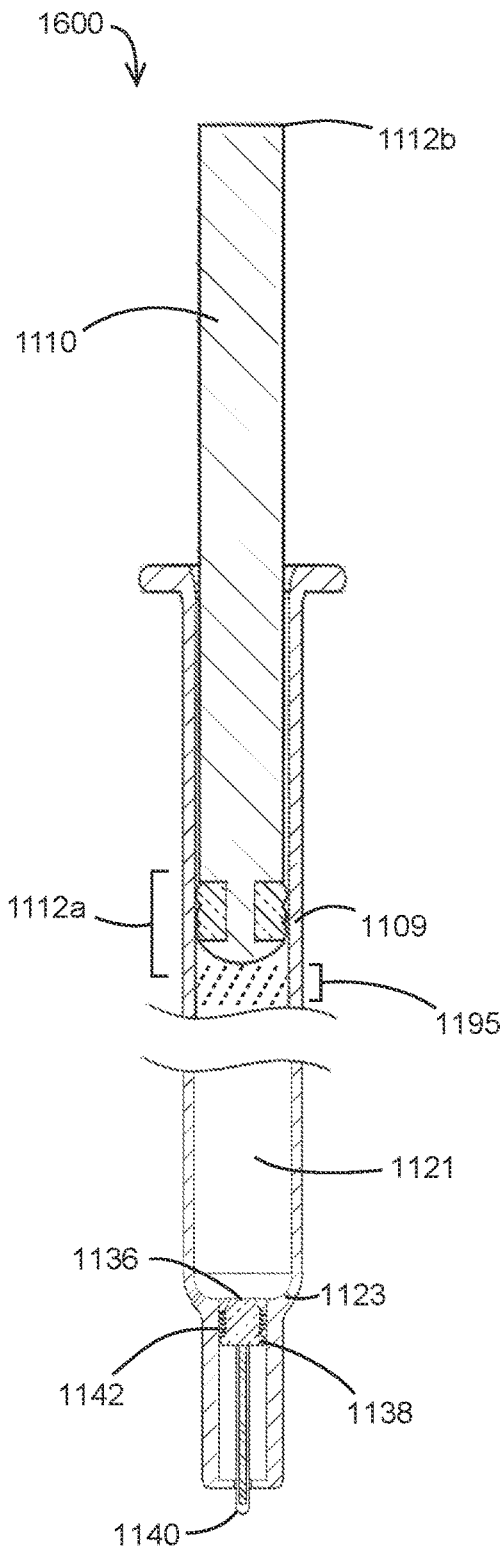
FIG. 25C
FIG. 25D

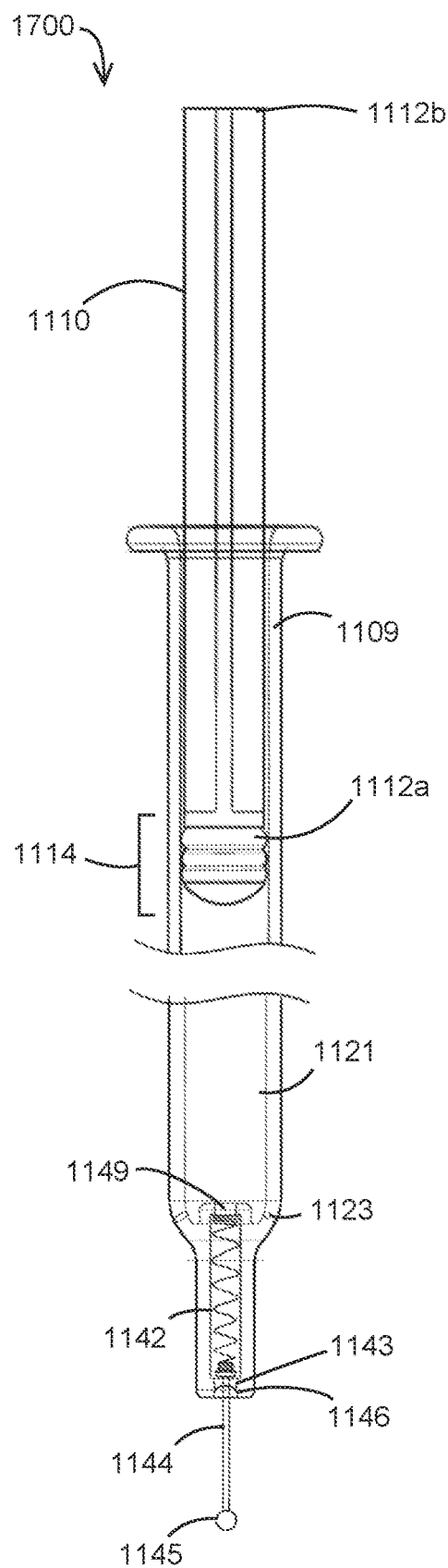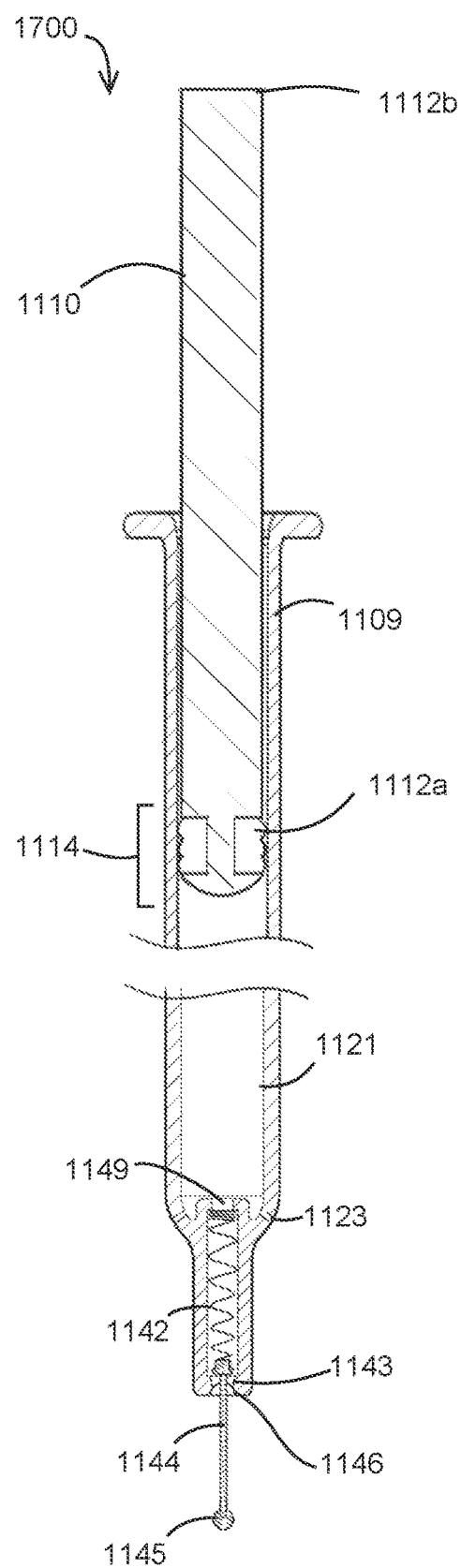
FIG. 26A
FIG. 26B

PREFILLED SYRINGE PLUNGER SIMULATION TRAINING DEVICE

BACKGROUND

Injectable medications are required for a number of varying illnesses and diseases. Many injectable medications require self-injection by a patient. Self-injection of a medicament using a device having a needle carries with it a certain stigma. Oftentimes users are weary of administering an injection for fear or anxiety related to handling an injection device, failing to deliver a complete dose of the medication, anticipated pain associated with injecting oneself, fear of accidentally sticking oneself with the needle during manipulation of the injection device, and difficulties in adequately grasping the dosing mechanism or injection device to inject oneself, among other concerns. An additional concern exists in instances in which users with little or no medical knowledge or experience are required to inject themselves or another subject using these devices. Moreover, the viscosities of medications vary from one medication to another. The viscosity of the medication being dispensed with an injection device has an effect on the amount of pressure needed to deliver the medication through the needle and into the subject. For those who are inexperienced in providing injections, or persons who are not familiar with the sensation related to the amount of pressure on a plunger of a prefilled syringe device needed to disperse medicament from a vial, through a needle, and into a patient would benefit from a training device designed to familiarize a user with this process. Moreover, familiarization with the sensations experienced during an injection with a medication having a particular viscosity. and requiring a certain amount of force and time to deliver the medication to the user would be beneficial in reducing the anxiety associated with delivering the medicament via injection, as well as ensuring an effective dose is delivered with the medicament delivery device.

SUMMARY

In an embodiment, an injection simulation device is provided including a housing defining a channel, the housing comprising a proximal end and a distal end, a plunger comprising a plunger rod body having a proximal end and a distal end and a stopper disposed at the distal end of the plunger rod, the plunger movable proximally and distally within the channel; and a friction feature associated with the housing, the friction feature for interfacing with the plunger rod, wherein the plunger moves in a distal direction relative to the housing to simulate medicament delivery and in a proximal direction to reset the injection simulation device, wherein the friction feature optionally causes differential resistance on the plunger rod, when the plunger rod moves in either the distal or proximal direction.

In other embodiments, an injection simulation device is provided including a housing defining a channel, the housing comprising a proximal end and a distal end, a plunger comprising a plunger rod having a proximal end and a distal end and movable proximally and distally within the channel, and a stopper at the distal end of the plunger rod, and a stopper protrusion member for creating a resistance on the stopper relative to the housing, wherein the stopper protrusion member optionally causes differential resistance on the stopper during movement of the stopper in either the distal or proximal direction.

In yet other embodiments, an injection simulation device is provided including a housing defining a channel, the housing comprising a proximal end and a distal end, an inner surface and an outer surface, a plunger comprising a plunger rod having a proximal end and a distal end and a stopper disposed at the distal end of the plunger rod, the plunger movable proximally and distally within the channel such that the stopper interfaces with the inner surface of the housing, and a surface texture region on the inner surface of the housing, the stopper, or the plunger rod, or a combination thereof, wherein the interface between the stopper or the plunger rod and the inner surface of the housing increases a coefficient of friction during movement of the plunger relative to the housing.

BRIEF DESCRIPTION OF THE DRAWINGS

A more particular description briefly stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which:

FIG. 3A-3B are side views of a proximal end of a partial view of an embodiment of an injection simulation device.

FIG. 5A is a side view of an embodiment of a plunger.

FIG. 5B-5C are cross sectional views of the plunger embodiment shown in FIG. 5A taken at X-X and Y-Y, respectively.

FIG. 6A is a side view of another embodiment of a plunger.

FIGS. 6B-6C are cross sectional views of the plunger in FIG. 6A taken at A-A and B-B, respectively.

FIG. 7 is a side view of another embodiment of a plunger.

FIG. 8A is a perspective view of a clip embodiment.

FIG. 8B is a perspective view of a housing embodiment of a device.

FIG. 8C is a cross-sectional view of the device embodiment shown in FIG. 8D.

FIG. 8D is a side view of an injection simulation device embodiment, the components of which are shown in part in FIGS. 8A-8C.

FIG. 9A is a side view of an embodiment of a clip.

FIG. 9B is a cross sectional view of the injection simulation device embodiment shown in FIG. 9C.

FIG. 9C is a partial perspective view of an injection simulation device embodiment.

FIG. 10A is a perspective view of an injection simulation device embodiment.

FIG. 10B is a partial cross-sectional view of the device embodiment shown in FIG. 10A.

FIG. 10C is an exploded view of a component of the device embodiment of FIG. 10A.

FIG. 10D is a partially assembled view of the component shown in FIG. 10C.

FIG. 11 is an exploded view of an injection simulation device embodiment.

FIG. 12A is a perspective view of a component of the injection simulation device embodiment of FIG. 11.

FIG. 12B is a side view of the component of the injection simulation device embodiment of FIG. 12A.

FIG. 12C is a cross sectional view taken at B-B of FIG. 12B.

FIG. 12D is a cross sectional view taken at A-A of FIG. 12B.

FIG. 14A is an exploded view of an embodiment of an injection simulation device.

FIG. 14B is a perspective view of a component of an injection simulation device embodiment.

FIG. 14C is a side view of the component of the injection simulation device embodiment shown in FIG. 14A.

FIG. 14D is a cross sectional view of the component taken at N-N of FIG. 14B.

FIG. 14E is a cross sectional view of the component taken at R-R of FIG. 14B.

FIG. 16A is a side view of an embodiment of an injection simulation device embodiment.

FIG. 16B is a cross sectional view of the injection simulation device embodiment shown in FIG. 16A taken at C-C.

FIG. 16C is a partial cross-sectional view of an injection simulation device embodiment taken at D of FIG. 16B.

FIG. 17A is a side view of an embodiment of the injection simulation device embodiment shown in FIG. 16A.

FIG. 17B is a cross sectional view of the injection simulation device embodiment shown in FIG. 17A taken at E-E.

FIG. 17C is a partial cross-sectional view of an injection simulation device embodiment taken at F of FIG. 17B.

FIG. 18A is a side view of an embodiment of the injection simulation device embodiment shown in FIG. 16A.

FIG. 18B is a cross sectional view of the injection simulation device embodiment shown in FIG. 18A taken at G-G.

FIG. 18C is a partial cross-sectional view of an injection simulation device embodiment taken at H of FIG. 18B.

FIG. 19A is a perspective view of an injection simulation device embodiment.

FIG. 19B is an exploded view of the injection simulation device embodiment in FIG. 19A.

FIG. 19C is a side view of the injection simulation device embodiment shown in FIGS. 19A-19B.

FIG. 19D is a cross-sectional view of the embodiment of the injection simulation device shown in FIG. 19C taken at section x-x of FIG. 19C.

FIG. 20A is a partial side view of a distal portion of a plunger embodiment.

FIG. 20B is a partial side view of the distal portion of the plunger embodiment shown in FIG. 20A.

FIG. 20C is a partial side view of a portion of a device embodiment.

FIG. 20D is a partial side view of a portion of the device embodiment of FIG. 20C.

FIG. 20E is a cross-sectional view of the embodiment shown in FIG. 20C.

FIG. 20F is a cross sectional view of the embodiment shown in FIG. 20D.

FIG. 20G is a cross sectional view of an alternative embodiment of a plunger.

FIG. 20H is another cross-sectional view of the alternative embodiment of the plunger rod shown in FIG. 20G.

FIG. 21A is a partial cutaway view of a device embodiment showing a distal portion of a device embodiment.

FIG. 21B is a cross-sectional view of the embodiment shown in FIG. 21A.

FIG. 21C is a partial cutaway view of a distal portion of the device embodiment shown in FIG. 21A.

FIG. 22A is a side view of a distal portion of a plunger embodiment.

FIG. 22B is a partial view of a portion of a protrusion of a plunger embodiment of FIG. 22A.

FIG. 22C is a side view of a distal portion of the plunger embodiment of FIG. 22A.

FIG. 22D is a partial view of a portion of a protrusion of a plunger embodiment of FIG. 22C.

FIG. 23A is a partial view of a device embodiment showing a distal portion of a plunger embodiment.

FIG. 23B is a cross sectional view of the portion device embodiment of FIG. 23A.

FIG. 23C is a cross sectional view of the portion device embodiment of FIG. 23A.

FIG. 24A is a partial cutaway view of a device embodiment showing an embodiment of a stopper protrusion.

FIG. 24B is a partial cutaway view of the device and stopper protrusion embodiment shown in FIG. 24A.

FIG. 24C is a partial cutaway view of the device and stopper protrusion embodiment shown in FIG. 24A.

FIG. 24D is a partial cutaway view of the device and stopper protrusion embodiment shown in FIG. 24A.

FIG. 24E is a partial cutaway view of the device and stopper protrusion embodiment shown in FIG. 24A.

FIG. 24F is a partial cutaway view of the device and stopper protrusion embodiment shown in FIG. 24A.

FIG. 25A is a partial cutaway view of an embodiment of an injection simulation device.

FIG. 25B is a cross sectional view of the embodiment of the device shown in FIG. 25A.

FIG. 25C is a partial cutaway view of the embodiment of the device shown in FIG. 25A.

FIG. 25D is a cross sectional view of the embodiment of the device shown in FIG. 25C.

FIG. 26A is a partial cutaway view of an embodiment of an injection simulation device.

FIG. 26B is a cross sectional view of the embodiment of the device shown in FIG. 26A.

DETAILED DESCRIPTION

The inventors have identified herein that it would be advantageous to simulate the tactility of a plunger during an injection with a prefilled syringe to set the expectations of a patient, and familiarize the patient with the forces that are sensed by a user during the delivery of medicament with a medicament-containing prefilled syringe used in an injection.

The inventors have discovered herein, embodiments of an injection training device used to simulate an injection device, wherein the device simulates an injection using drugs of varying viscosities, for example. The injection simulation device embodiments provided herein simulate an injection experience for a user, such that a user senses the resistance(s) felt during injection with an injection device and a drug having a certain viscosity. The injection simulation device embodiments described provide for resistance applied to a plunger of the device, in some non-limiting embodiments, and ease of reset of the device for subsequent use in non-limiting embodiments.

Figure 1:
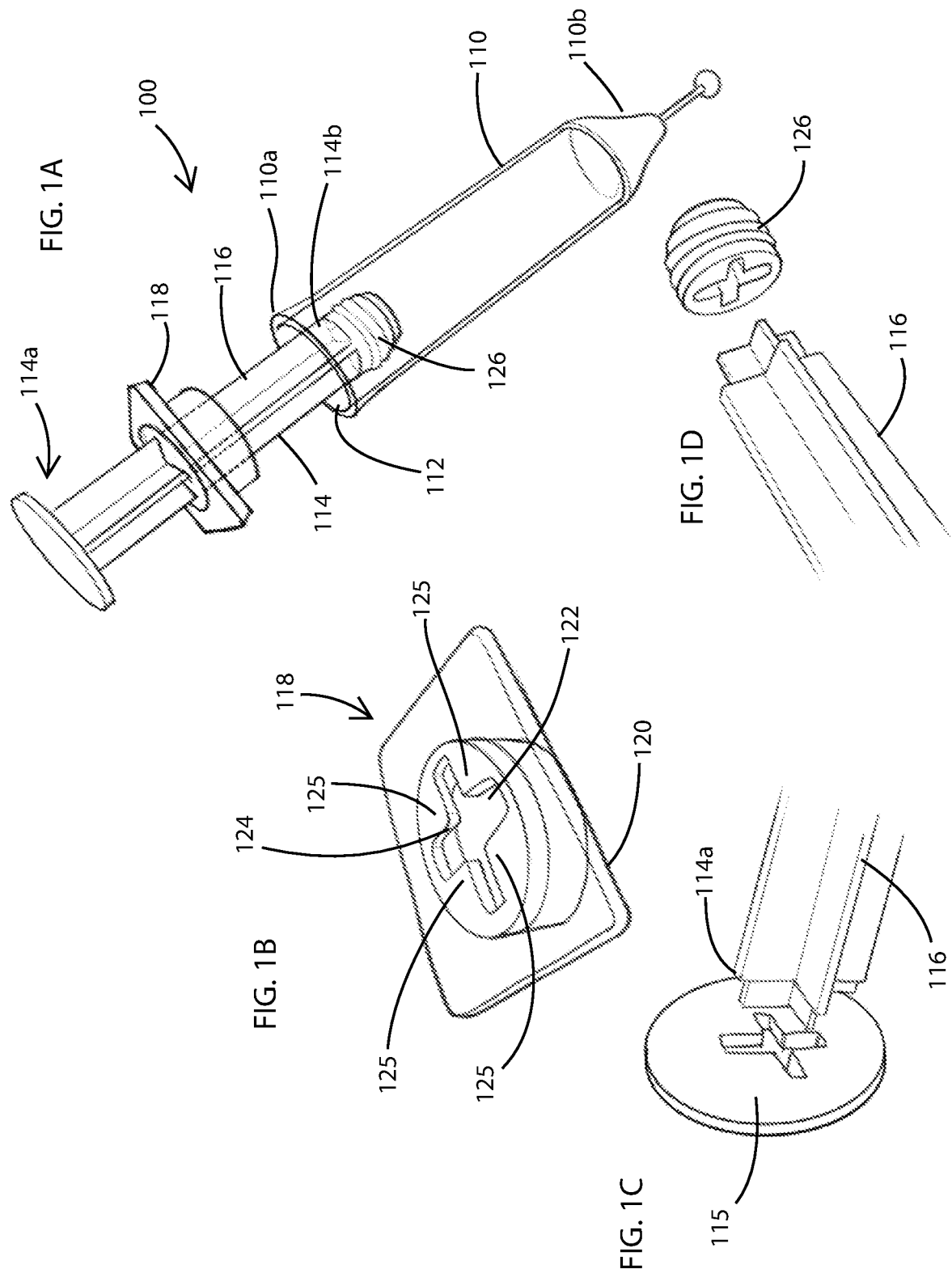
FIG. 1A is a perspective view of an embodiment of an injection simulation device.
FIGS. 1B-1D include perspective views of components of the embodiment of the device in FIG. 1A.

FIG. 1A is a perspective view of an embodiment 100 of an injection simulation device including a housing 110 having a proximal end 110a and a distal end 110b, and defining a channel 112 there within. The device 100 further includes a plunger 114 having a proximal end 114a and a distal end 114b, and a plunger rod 116 extending therebetween. The embodiment 100 shows a stopper 126 attached to the distal end of the plunger 114b. Disposed on the plunger rod 116 is a flange portion 118. The flange portion 118 is further shown in the perspective view of FIG. 1B. The flange portion 118 includes a flange outer portion 120, an opening 122, and a friction feature 124. In some non-limiting embodiments, the friction feature 124 may be positioned at or near the opening of the flange portion.

The flange portion 118 may define an opening 122 of various shapes. Shown here is a cross-shaped opening; however, the opening is not limited to a cross shape. The opening 122 may be circular, square, triangular, or any other shape. The shape of the opening 122 may compliment the profile of the plunger rod 116, as shown herein, to allow the plunger rod 116 to slide relative to the opening 118 during movement of the plunger 114 within the channel 112 of the housing 110. During movement of the plunger 114 toward the distal end of the housing 110b, the interface between the friction feature 124 and the plunger rod 116 increases a resistance on the plunger rod 116 movement, in one non-limiting embodiment. The friction feature 124 may include a number of friction flaps 125 as shown in FIG. 1B. The friction flaps 125 may be formed with any material; however, in one non-limiting embodiments the friction flaps 125 may be formed, at least in part, of a flexible material to allow the flaps 125 to flex or bend during movement of the plunger 114, and in a further, non-limiting embodiment, during movement of the plunger 114 in the proximal direction (i.e. during reset of the plunger 114). In non-limiting embodiments, the plunger rod 116 may be cross-shaped as shown in a non-limiting example in FIG. 1A, cylindrical as shown in another non-limiting example in FIG. 10A, or any other shape. The plunger rod 119 may include a generally continuous width from proximal end 117a to distal end 117b as shown in an alternative, non-limiting plunger embodiment example 117 in FIG. 2

FIG. 1C shows the proximal end of the plunger 114a and a contact member 115 at the proximal end. The contact member 115 is the point at which a user presses the plunger 114 to move the plunger 114 toward the distal end of the housing 110b, in one non-limiting embodiment. FIG. 1D shows the distal end of the plunger rod 116 and the stopper 126, which may be removably or permanently associated therewith.

In some non-limiting embodiments provided herein, the force profile simulated by the injection simulation device may include a breakaway force characterized by an initial greater resistance followed by a glide force with a lower resistance relative to the breakaway force. The differences in resistance may be possible due to the friction feature, in one non-limiting embodiment, which may simulate, at least in part, the breakaway force in one example.

Figure 2:
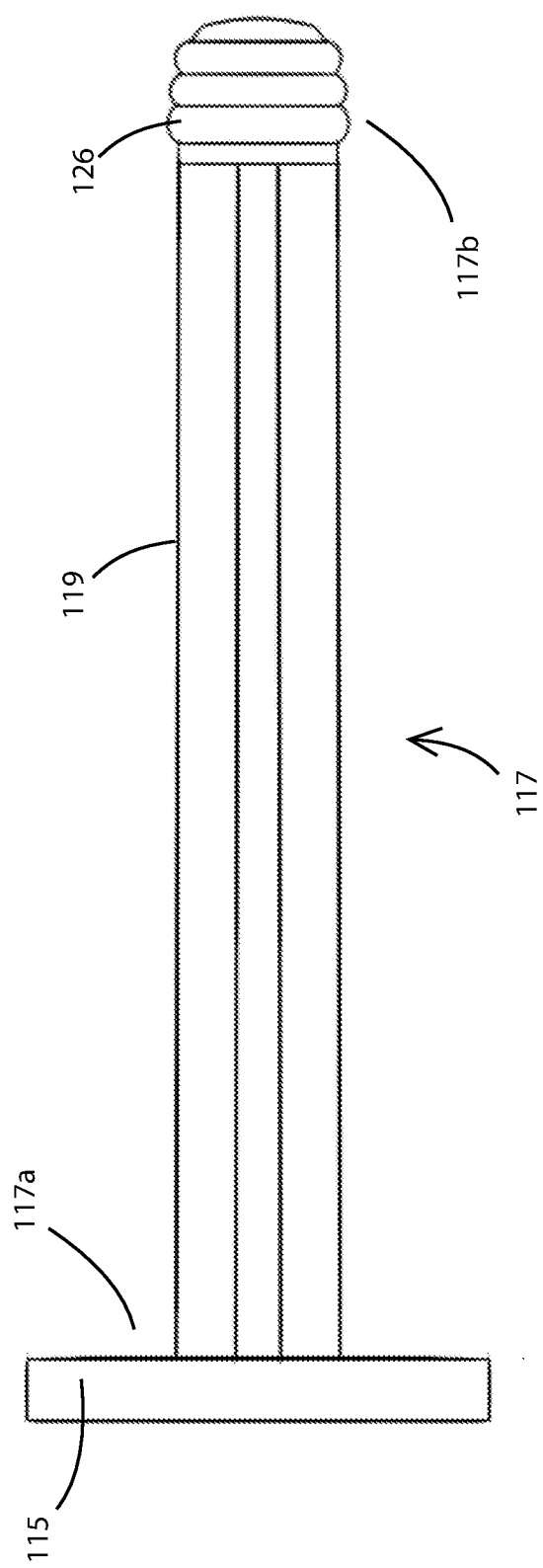
FIG. 2 is a side view of an embodiment of a plunger.
Figure 4:
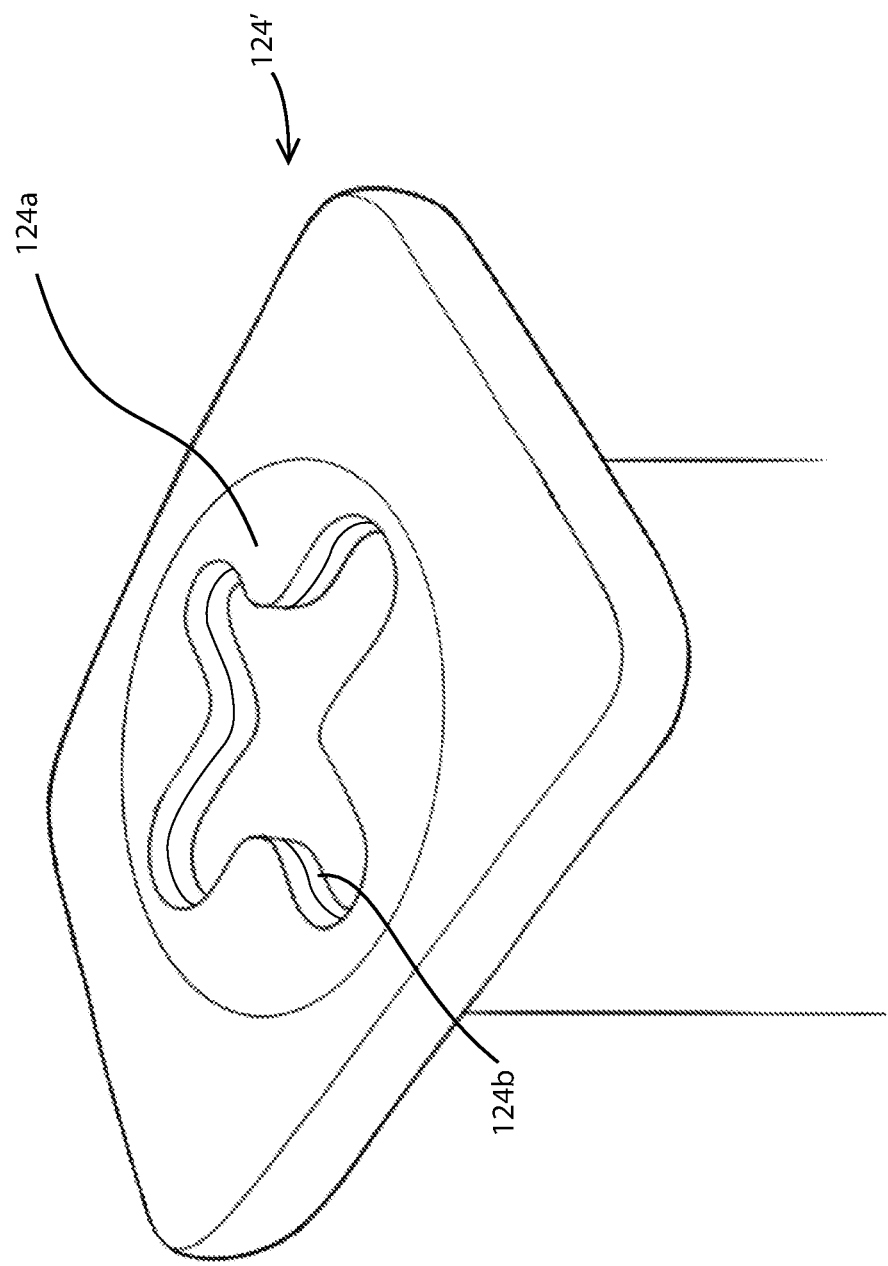
FIG. 4 is a proximal view of an embodiment of a friction feature.

FIG. 2 shows a plunger 117 embodiment including a plunger rod 119 having a cross-shape, wherein the proximal end 117a is substantially the same width as the distal end 117b. A stopper 126 is shown at the distal end of the plunger 117b, and a contact member 115 is disposed at the proximal end of the plunger rod 117a.

FIG. 3A-3B demonstrates an interface between a plunger rod 119 of a plunger 117 and a friction feature 124' during distal (FIG. 3A) and proximal (FIG. 3B) movement, in a non-limiting embodiment. During distal movement of the plunger rod 119, the contact between the rigid material 124b of the friction feature 124' and the flexible material 124a of the friction feature 124' and the plunger rod 119 resistance on the plunger 119 is increased. During proximal movement of the plunger 117 (FIG. 3B), the flexible material 124a flexes to provide a relief, such that resistance on the movement of the plunger 117 decreases, due to the decrease in contact between the friction feature 124' and the plunger rod 119. In some non-limiting embodiments, as shown in FIGS. 3A-3B, a space 127 between the rigid material 124b and the plunger rod 119 may be provided to assist in relieving the resistance during proximal plunger 117 movement. A close-up of the friction feature 124' shown in FIGS. 3A-3B demonstrates there may be a small overlap of the flexible material 124a (or flexible flaps), over the rigid material 124b to provide for increase resistance on the distal movement of the plunger 117 and decrease resistance on the proximal movement of the plunger 117, in some non-limiting embodiments.

FIGS. 5A-C and FIGS. 6A-C show different embodiments of the plunger rod 114, 114'. In FIG. 5, a side view of a plunger rod 116 having a cross shaped profile is shown. The width B of each cross member 154 of the plunger rod 116 is substantially equivalent as seen in FIGS. 5B, 5C. FIG. 5B includes a cross-section taken at X-X of FIG. 5A adjacent to the proximal plunger end 114a, and FIG. 5C includes a cross section taken at Y-Y of FIG. 5A adjacent to the distal plunger end 114b. A first width F of the plunger rod 116 is substantially equivalent from the proximal end 114a to the distal end 114b, however, a second width D, E, of the plunger rod is greater (D) adjacent to the proximal plunger end 114a, and smaller (E) adjacent to the distal plunger end 114b, in one non-limiting embodiment. In the embodiment shown, the second width of the plunger rod 116 decreases from the proximal end 114a to the distal end of the plunger 114b. The varying dimensions of the components of the plunger rod can be used to control the force required to move the plunger relative to the housing and to simulate an injection, or to reset the device. A resistance nodule or breakaway feature 113 may be provided on a portion of the plunger rod 116 to simulate a breakaway force of an injection device. The breakaway feature 113 interfaces with an inner surface of the housing 110 of the injection simulation device provides a resistance on the movement of the plunger 114 to simulate the breakaway force sensed during an injection with an injection device containing medicament.

FIG. 6A-C shows an embodiment of a plunger rod 116' wherein a first width F of the plunger rod 116' is substantially equivalent at the proximal plunger end 114a and the distal plunger end 114*b*, and a second width C of the plunger rod 116' is substantially equivalent at the proximal plunger end 114*a* and the distal plunger end 114*b*. In the embodiment shown in FIGS. 6A-B (FIG. 6B is a cross section taken at A-A of FIG. 6A and FIG. 6C is a cross section taken at B-B of FIG. 6A). One or more of the cross members 157 of the plunger rod 116' may include a width A that is larger near the proximal plunger end 114*a*' than a width B of the cross member 157 near the distal plunger end 114*b*' as shown in FIG. 6A. The variation in the width of the cross members 157 may affect the directionally-controlled resistance on the plunger 114 during movement of the plunger relative to the housing 110 of the injection simulation device, in a non-limiting embodiment. The resistance may be caused by the interface between a portion of the plunger and an inner surface of the housing via increased and decreased surface contact, or by interaction with a friction feature as described herein.

In yet another embodiment shown in FIG. 7, the plunger rod 145 may include a taper wherein the width of the plunger rod 145 allows simulation of the force profile of an injection device including breakaway force (section 3), glide force (section 2) and delivery of medicament force (section 1). Once past the breakaway section (section 1) and the glide section (section 2), the resistance on the plunger rod 145 increases during distal movement of the plunger relative to the housing as shown in section 1 of the tapered plunger rod profile in FIG. 7, to simulate various viscosities of medicament encountered in an injection device.

FIGS. 8A-D provides an embodiment 200 in which a clip 424 is provided including, having one or more protrusions 426 on an inner surface thereof for interfacing with a plunger 218 of a device 200. An interface between the protrusions 426 and the plunger rod 218 may cause a resistance on the movement of the plunger rod 218. The resistance may be directionally controlled by altering the profile of the plunger rod 218. For example, as described in other embodiments herein, wherein the width of the plunger rod 218 itself increases from distal end to proximal end, the resistance during distal movement of the plunger rod will increase, and during proximal movement will decrease. In other embodiments, the profile of each cross member may be altered as shown in FIG. 6 to control the resistance on plunger movement. The one or more protrusions 426 may traverse apertures 422 in the housing 410 of the device shown in FIG. 8B, in one non-limiting embodiment. The housing 410 may include a housing flange 411 at or near its proximal end. The clip body 428, then surrounds a portion of the device housing 410 surface. Upon proximal movement of the plunger 214, the protrusions 426 contact the plunger rod 218, and may cause resistance during plunger 214 movement in some embodiments. The plunger 214 may also include a stopper 216 at its distal end. In some embodiments, the proximal movement of the plunger 214 may be limited by the interface between the stopper 216 and the clip 424, preventing removal of the plunger 214 from the device housing 410. In some non-limiting embodiments, the interface between the protrusions 426 and the plunger rod 218 limits or prevents axial rotation of the plunger 214.

FIGS. 9A-C provide views of yet another embodiment 300 of an injection simulation device including a clip 524 with a clip body 528 and a protrusion 526 having a pinching feature. The protrusion 526 may extend through an aperture 522 (not shown) in the device housing 510 to contact the plunger rod 218, wherein upon movement of the plunger 214, resistance may be caused by the interface between the protrusion and the plunger rod 218 as seen in FIGS. 9B-9C. Furthermore, proximal movement of the plunger 214 may be limited by the interaction between the clip 524 and the stopper 216. Plunger 214 removal from the device housing 510 may be prevented in this manner. Axial rotation of the plunger 214 may limited or prevented by the interface between the protrusion 526 and the plunger rod 218. Interface between the protrusion 526 and the plunger rod cross member 154 may increase resistance on the movement of the plunger. In some non-limiting embodiments, for example when the plunger rod cross member width varies from proximal end to distal end as shown in FIGS. 6A-C, the resistance on the movement of the plunger may vary between distal plunger movement and proximal plunger movement.

FIGS. 10A-D includes yet another embodiment in which a device 600 includes a plunger 614, movable within a chamber 612 of a device housing 610. The device housing 610 includes a proximal end 610*a* and a distal end 610*b*, and a flange at or near its proximal end 611. The plunger 614 may include a cylindrical shaped plunger rod 618, in a non-limiting embodiment, and a stopper 616 at or near its distal end. The plunger 614 may include an at least partially hollow or solid plunger rod (solid plunger rod shown in FIG. 10B). In some embodiments the diameter of the plunger rod 614 may differ at the proximal end and at the distal end of the plunger. In one example, the plunger rod may include a greater diameter near its proximal end and a smaller diameter near its distal end. The plunger may taper from the proximal end to the distal end in some embodiments. In other embodiments, the plunger may include a rod having a larger diameter at its distal end, and a smaller diameter at its proximal end. The plunger may taper from the distal end to the proximal end in, some embodiments. In other embodiments, the diameter of the plunger rod may be substantially consistent from the proximal end to the distal end. The flange 611 may include or be associated with an annular member 609, which in some examples may include a toroidal or cannulated spring, an o-ring, or other annular device. The annular member 609 may be formed as part of the flange 611 or may be associated therewith in some embodiments. Upon assembly of the device, the annular member 609 and flange 611 may be placed on the plunger rod 618 or at the proximal end of the device housing 610, such that during movement of the plunger 614 in the proximal direction the stopper 616 abuts a portion of the flange 611, for example, a lower surface of the flange 607 within the chamber 612, preventing removal of the plunger 614 from the device housing 610, for example. In some embodiments, a pocket 613 may be provided either on the plunger rod 618 (not shown in FIG. 10B) or in the device housing 610 as shown in FIG. 10B, or even in the flange body 611 for resting and/or containing of at least a portion of the annular member 609. The annular member also provides a resistance mechanism to confer resistance to the plunger 614 during movement of the plunger relative to the housing 610. This feature may be used to simulate an injection device for training purposes. In some non-limiting embodiments, resistance may be greater during distal movement of the plunger (movement toward the distal end of the device housing 610*b*), and lesser during plunger reset (i.e., during proximal plunger movement). The proximal plunger movement may also be restricted or limited at different points along the device, for example, at a predetermined fill line, in order to mimic or simulate the fill line reset of an injection device. In other non-limiting embodiments, the plunger rod may decrease in diameter from the proximal plunger rod end to the distal plunger rod end, such that resistance on the distal movement of the plunger relative to the housing may be greater than the resistance during proximal movement of the plunger, to provide a simulated injection, and allow for ease during reset of the device.

In the embodiment shown in FIG. 10A-D, the resistance may be caused by the interface between the annular member 609 and the plunger rod 618 as the rod 618 moves relative to the housing 610. The pocket 613 may be shaped such that the annular member is maintained within the pocket 613 during distal movement of the plunger 614, but that the annular member is released from the pocket 613 during proximal movement of the plunger to decrease resistance on the proximal plunger movement during reset of the device, in some embodiments.

In some non-limiting embodiments herein a friction feature is described. The friction feature may be one component or a combination of components. The friction feature may relate to the movement of one component relative to another, or movement of two or more components relative to one another.

In one non-limiting example, the friction feature may include one or more protrusions as shown in FIG. 8A and FIG. 8C, for example, wherein the interface between the protrusions 426 and a portion of the plunger rod 118 as they move relative to one another causes a resistance on the plunger rod during movement of the plunger 114. In some embodiments, the resistance may be greater in one direction of movement of the plunger than in the opposing direction. This differential resistance may be caused by a particular shape of the protrusion causing more resistance in one direction and less resistance in the opposing direction, in a non-limiting embodiment. In other embodiments, this resistance differential may be caused by the profile of the plunger ord. In non-limiting examples, the plunger rod may include embodiments as shown in FIGS. 5A, 6A, 12A, 14B, therefore the interface between the friction component during movement of the plunger relative to the housing may cause a differential resistance on the plunger rod during movement. Moreover, a combination of a variation of the shape of the protrusion(s) and a variable profile of the plunger rod as shown in the non-limiting examples of FIGS. 5A, 6A, 12A, 14B, may cause a differential resistance on the plunger rod during movement.

In another example, shown in FIG. 1A-1D the friction feature may include one or more flap members disposed in an opening of a flange, such that movement of the plunger relative to the friction feature causes a resistance on the movement of the plunger as described herein. However, in other non-limiting embodiments, the friction feature may not cause a differential resistance on the plunger rod during movement in either the proximal or distal direction. In some instances, the resistance on the plunger rod may be substantially equal regardless of the direction of movement.

FIG. 11 is an exploded view of an injection simulation device embodiment 800, including a housing 810, and a plunger 814 for being received there within, the plunger 814 comprising a plunger rod 818 comprising a core 813 and a number of cross members 815. Each of the cross members 815 comprising a profile for allowing the simulation of forces of an injection device as the plunger 814 is moved relative to the housing 810, due to the friction feature 816. The friction feature 816 includes a friction component 824 and an annular member 826. When assembled, the annular member 826, which may be an o-ring or other annular member as described in other embodiments herein, or known to those skilled in the art, is held within the friction component 824, and the plunger rod 812 slides within the opening of the friction feature 816, such that the cross members 816 interface with the annular member 826 as the plunger rod 812 slides therethrough, creating a resistance on the plunger 814. As a plunger rod protrusion 817, shown in FIG. 11, interfaces with the annular member 826, an increased friction on the plunger 814 movement occurs as the plunger is moved distally, to simulate a break out glide force sensed during operation of an injection device. Following the initial break out glide force resistance during movement of the plunger protrusion 817 relative to the annular member 826, the resistance on the plunger 814 decreases slightly as the plunger rod 812 is further moved distally relative to the housing 810. Continued movement of the plunger 814 distally within the housing 810 causes an increase in resistance on the plunger 814 as the profile of the cross members 815 changes toward the proximal end of the plunger rod 812.

FIG. 12A is a perspective view of the plunger 814 having a plunger rod 818 and a stopper 812, the plunger rod 818 comprising a proximal end 818a, a distal end 818b, a core 813 and a number of cross members 815 extending between the proximal and distal end 818a, 818b. Shown in FIG. 12A is a plunger rod protrusion 817 configured to simulate a break out glide force when the plunger rod protrusion traverses the friction feature 816 upon distal movement of the plunger 815 relative to the housing 810. FIG. 12B is a side view of the plunger 814 having a plunger rod having a proximal end 818a and a distal end 818b. The plunger rod 818 comprising a plurality of cross members 815, each cross member comprising a profile to cause a resistance on the plunger movement relative to the housing (housing not shown in FIG. 12B). Plunger rod section 850 simulates a puncture and/or breakaway force, wherein section 852 simulates a glide force, and section 854 simulates a delivery of medicament force as these portions of the plunger rod contact the friction feature 816 (not shown in FIG. 12B). FIG. 12C includes a cross sectional view of the plunger rod 814 taken at B-B of FIG. 12B, wherein cross members 857 are shown, along with core 813, and stopper 812, and in FIG. 12D a cross section of the plunger rod 814, taken at A-A of FIG. 12B can be seen, showing cross members 857, the stopper 812, and the core 813. As can be seen from the cross-sectional views in FIGS. 12C-12D, a height G of the cross members 857 is larger near the proximal end 818a of the plunger rod, than at the distal end 818b of the plunger rod, such that resistance increases as the plunger rod 814 moves distally relative to the friction feature 816.

Figure 13D:
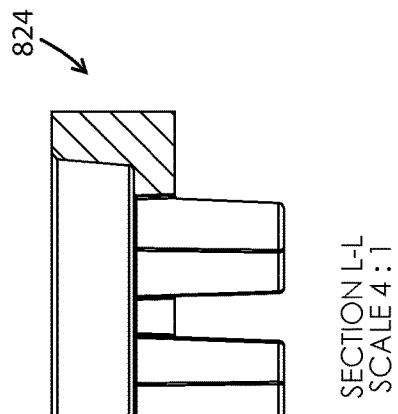
FIG. 13D is a top side view of a component of FIG. 13A.
Figure 13C:
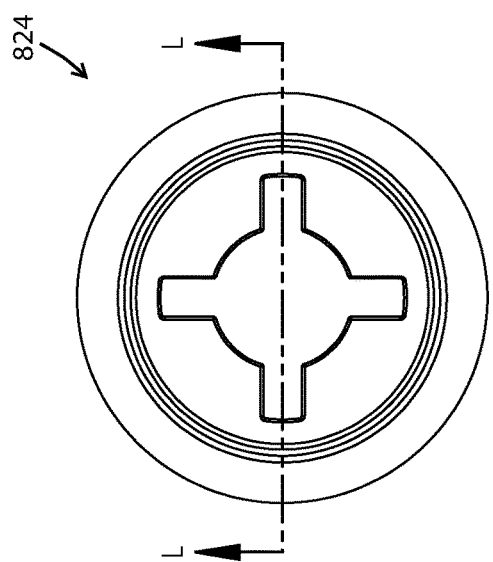
FIG. 13C is a cross sectional view of a component of FIG. 13A taken at L-L of FIG. 13C.
Figure 13A:
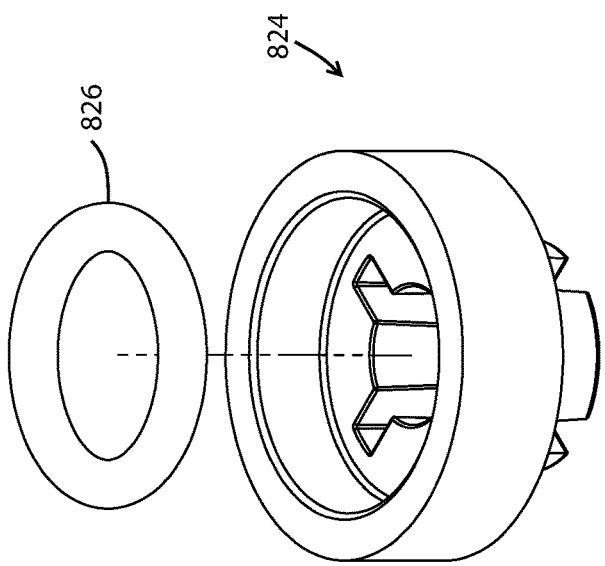
FIG. 13A is an exploded view of a component of the injection simulation device embodiment of FIG. 12A.
Figure 13B:
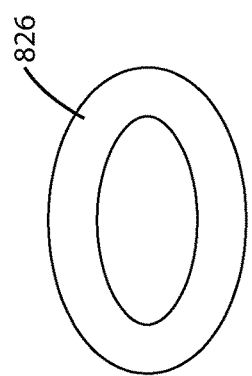
FIG. 13B is a perspective view of an annular component shown in FIG. 13A.

FIG. 13A is an exploded view of a friction feature 816 embodiment, comprising an annular member 826 and a friction component 824 for maintaining the annular member 826 there within. The friction component 824 includes a friction component opening as shown, configured to receive a plunger rod. FIG. 13B is a perspective view of an annular member 826 embodiment. FIG. 13C is a top side view of the frictional component 824 embodiment showing the opening for receiving the plunger rod. FIG. 13D is a cross sectional view of the friction component 824 embodiment showing an inset portion 825 for receiving the annular member 826, (shown in FIG. 13B). The cross-sectional view of the friction component 824 of FIG. 13D is taken at L-L of FIG. 13C.

Figure 12E:
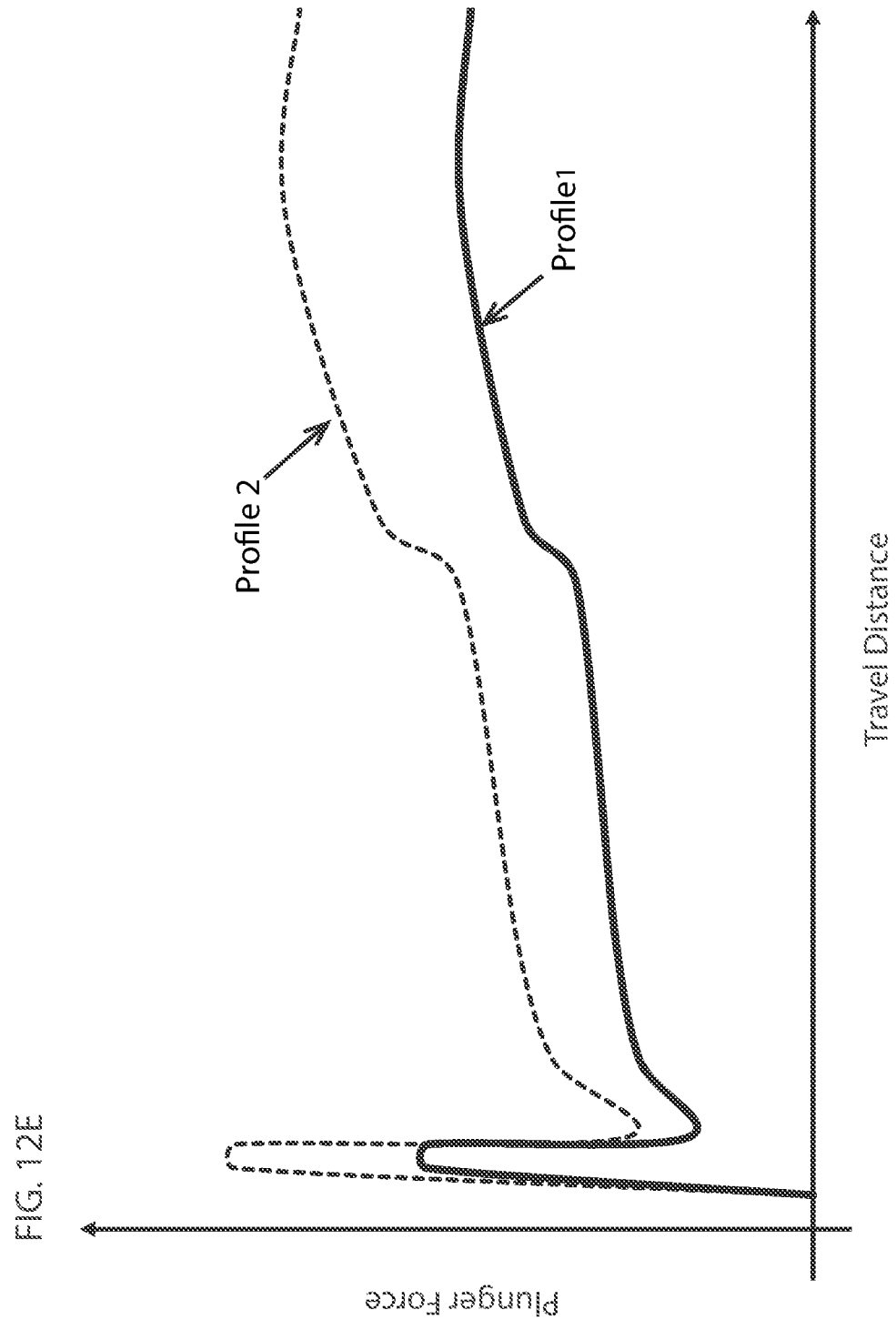
FIG. 12E is a graphical illustration of two plunger rod profiles, in a force versus travel distance illustration.

FIG. 14A is an exploded view of an embodiment of an injection simulation device 800'. FIG. 14B is a perspective view of a plunger 814 embodiment, including a plunger rod 818' and a stopper 812, wherein the plunger rod 818' includes a proximal end 818a' and a distal end 818b', and a number of cross members 815' and a core 813'. The cross members 815' may include a profile to simulate forces sensed during an injection with an injection device, including, but not limited to puncture force(s), break out glide force(s) (BOGF), insertion force(s), and/or removal force(s) as shown in FIG. 14B-14C. FIG. 14C is a side view of the plunger 814' showing an embodiment of the profile of the cross member 815', which extends from the proximal end 818a' to the distal end 818b' of the plunger rod 818. The plunger protrusion 817' disposed near the distal end may simulate a BOGF during a simulation with the device. Similar to FIG. 12B, various sections of the plunger rod 818 simulate various resistances as the rod is moved distally toward the housing 810, wherein generally a resistance on the rod increases with distal movement. FIG. 14D-14E are cross-sectional views of the plunger rod embodiment 818' taken at sections N-N and R-R of FIG. 14C, respectively. In both FIGS., the stopper 812 can be seen, and the core 803 and cross members 857' of the plunger rod 818' embodiment are shown. Near the proximal end, the cross members 857' include a height E, which is larger than the height E at near the distal end (shown in FIG. 14E). This allows for an increase in resistance on the plunger rod 818' as the plunger 814 is moved distally relative to the housing 810, due to the interaction between the cross members 857' and the friction feature 816. The cross members in the plunger embodiment 814' shown in FIG. 14A-E, as compared to the cross members of the plunger embodiment 814 shown in FIGS. 12A-D differ in width. The cross members 857 are narrower than the cross members 857'. The non-limiting embodiments shown provide examples of varying heights and widths for the cross members to affect an overall difference in the resistance applied to the plunger during use of the device. As the cross members widen, as in embodiment 814', a greater force is required to move the plunger distally relative to the housing, and therefore, by virtue of movement of the plunger distally relative to the housing, a greater resistance is placed on the plunger rod, due to an increase in surface area contact between the plunger rod and the friction feature (i.e., the annular member in embodiments 800, 800'). A comparison of plunger force versus plunger travel distance for two different plunger profiles is shown in the illustrative graph of FIG. 12E. In FIG. 12E, for example, the plunger rod of Profile 2 may include one or more wider cross members, requiring a greater plunger force for movement, whereas a plunger rod of Profile 1 may include one or more narrower cross members as compared to the plunger of Profile 2, requiring a lesser relative force for plunger movement.

Figure 15D:
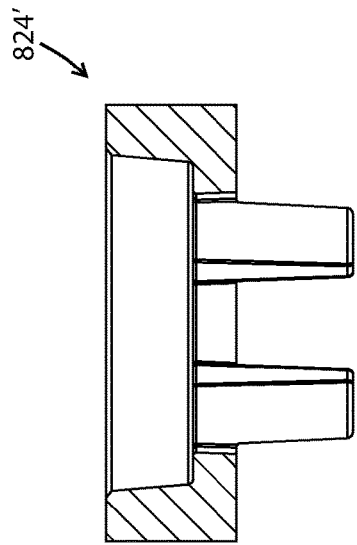
FIG. 15D is a cross sectional view taken at section V-V of FIG. 15D.
Figure 15C:
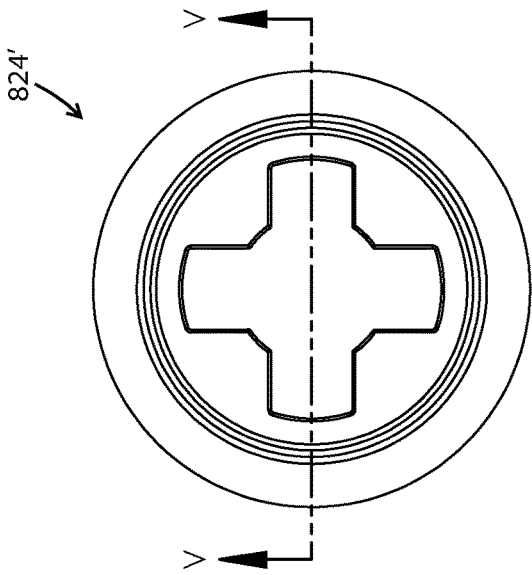
FIG. 15C is a top view of a friction component embodiment.
Figure 15A:
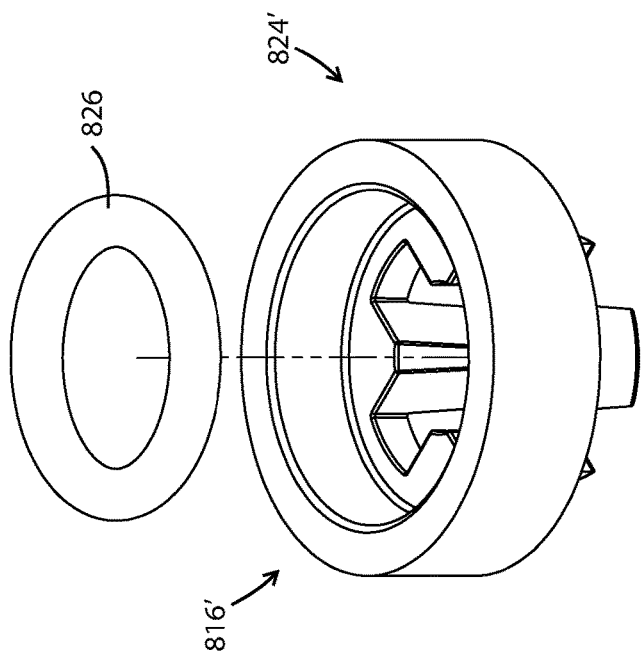
FIG. 15A is an exploded view of a friction feature embodiment.
Figure 15B:
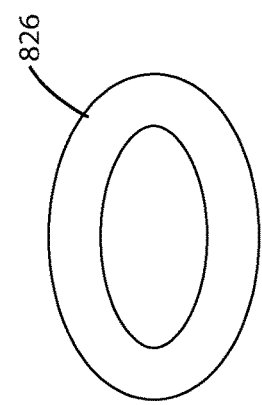
FIG. 15B is a perspective view of an annular member embodiment.

FIGS. 15A-D include various views of a friction feature 816' having a friction component 824' and an annular member 826. The exploded view of FIG. 15A provides the annular member 826 and the friction component 824' for receiving the annular member. An opening for receiving a plunger rod 818' is shown in FIG. 15A. FIG. 15B is a perspective view of the annular member 826. FIG. 15C is a top view of the friction component 824' showing the opening for receiving the plunger rod 818'. FIG. 15D is a cross-sectional view of the friction component 824' taken at section V-V of FIG. 15C, wherein the inset portion 825' for receiving annular member 826 is shown.

FIG. 16A is a side view of an injection simulation device embodiment 800 including a housing 810 and a plunger 814. FIG. 16B is a cross sectional view of the embodiment 800 taken at section C-C of FIG. 16A, wherein the friction feature 816 is shown. Friction feature 816 includes friction component 824 and annular member 826. In some embodiments, the friction feature 816 may be removable from the housing 810, in other embodiments the friction feature 816 may be affixed onto the housing 810, in yet other embodiments, the friction feature 816 may be formed as part of the housing 810. The plunger 814 is shown in FIG. 16B as partially within the friction feature, such that the plunger protrusion 817 is adjacent to the annular member 826, further distal movement of the plunger 814 would increase resistance on the plunger rod due to the interface between the plunger protrusion 817 and the annular member 826. FIG. 16C is a partial cross-sectional view of the device 800, showing the position of the annular member 826 relative to the plunge protrusion 817.

FIGS. 17A-C provide side, cross-sectional and partial cross-sectional views of the embodiment 800 shown in FIGS. 16A-C, wherein the plunger 814 is further moved distally relative to the housing 810, such that the plunger protrusion 817 has traversed the annular ring 826 as shown in the cross-sectional view of FIG. 17B, taken at section E-E of FIG. 17A. The profile of the plunger 814 including sections 854, 852, and 850 for simulating breakout glide force and insertion force are shown in FIG. 17B. FIG. 17C is a partial cross-sectional view of FIG. 17B.

FIGS. 18A-C provide side, cross-sectional and partial cross-sectional views of the embodiment 800 shown in FIGS. 16A-C and 17A-C, wherein the plunger 814 is yet further inserted into the housing 810 and the plunger 814 is entering the "delivery of medicament force" simulation section, section 854, wherein a resistance on the plunger movement will increase as the annular member 826 moves from section 852 to section 854 of the plunger rod to simulate the forces sensed during the delivery of medicament. As the diameter of the plunger rod increases, as shown in FIGS. 16A-18C, the resistance created during movement of the plunger in the distal direction can increase. In some non-limiting embodiments discussed herein, upon applied pressure on the annular member 826, the annular member may deform, or become compressed as different pressures are applied thereto.

FIG. 19A provides a perspective view of an injection simulation device embodiment having a housing 1109 and a plunger 1110 having a proximal end 1120B and a distal end 1120A. The housing 1109 forming a channel 1121, wherein the plunger 1110 may slide relative to the housing 1109, within the channel 1121, in some, non-limiting embodiment. The housing may include a proximal end 1119a and a distal end 1119b. The plunger 1110 may be inserted into the channel 1121 at the proximal end 1119a of the housing 1109 and may be slidable in a distal direction toward the distal end of the housing 1119b, in a non-limiting embodiment. FIG. 19B shows an exploded view of the injection simulation device embodiment provided in FIG. 19A, with the plunger 1110 removed from the channel 1121 of the housing 1109. FIG. 19C is a side view of the injection simulation device embodiment shown in FIGS. 19A-19B, and FIG. 19D is a cross-sectional view of the embodiment of the injection simulation device shown in FIG. 19C taken at section x-x of FIG. 19C. The distal end 1120 of the plunger 1110 is the portion shown in various embodiments in FIGS. 20-25. In the embodiment shown in FIGS. 19A-D, at least one protrusion 1114 is provided at the distal end of the plunger 1110.

In a first embodiment 1100 shown in FIG. 20A-F a plunger embodiment 1110a is provided having a proximal end (not shown in FIG. 20) and a distal end 112a, and at least one protrusion 1122A disposed near the distal end 1120A. During movement of the plunger 110a in a distal direction, as shown by the arrow in FIG. 20A, the at least one protrusion 1122A expands laterally as shown in FIG. 20B, increasing a contact between the protrusions 1122A and a housing 1109 as shown in FIG. 20C, of an injection simulation device 1100. Consequently, a friction is increased on the movement of the plunger 1110a during movement in the distal direction. The housing 1109 has an inner surface 1109a and an outer surface 1109b, and the plunger 1110a may slide relative to the housing 1109, such that the at least one protrusion 1122A interfaces with the inner surface 1109a of the housing.

Movement of the plunger 1110a in a proximal direction as shown by the arrow in FIG. 20, causes the protrusions 1122A to move inward (i.e., to retract), as shown in FIG. 20D, such that the friction between the protrusions 1122A and an inner surface 1109a of the housing within which the plunger 1110a may slide is decreased. Movement of the plunger 1110a in the proximal direction as shown in FIG. 20C-D resets the plunger 1110a for a subsequent use. The protrusions 1122A may be provided on a distal portion of the plunger 1110a in one embodiment. In another embodiment, the protrusions 1122A may be provided on a stopper associated with the plunger distal end 1120A. FIGS. 20E-F include cross sectional views of the plunger embodiment 1110a shown in FIGS. 20A-B, demonstrating movement of the plunger 110a in the distal direction. A portion of the plunger 1110a, the plunger rod portion 1113 is viewable in FIGS. 20E-F.

An alternative embodiment 1150 of a plunger embodiment 110a' is provided in FIG. 20 G-20 H, wherein the at least one protrusion 1122A is movable relative to the plunger 1110a'. In one non-limiting embodiment, the at least one protrusion 1122A may be slidable relative to the plunger 1110a' between a first position as shown in FIG. 20G and a second position as shown in FIG. 20F. The at least one protrusion 1122A may not be further slidable once the protrusion 1122A interfaces with the protrusion interfacing surface 1111. In non-limiting embodiments, the plunger embodiments described herein may include different shapes, sizes, and/or surface textures. In one non-limiting embodiment, the plunger 1110a' may include a plunger rod portion 1113' having a variable cross sectional surface area from proximal end 1120B to distal end 1120A. In one non-limiting embodiment, the cross-sectional surface area of the plunger rod portion 1113' or any portion of the plunger 1110a' for example, may decrease between the protrusion interfacing surface 1111 and the distal end of the plunger 1120A, for example. In the embodiment shown in FIG. 20G-20H, the plunger rod portion 1113' decreases in cross sectional surface area between the protrusion interfacing surface 1111 and an area adjacent to the distal end of the plunger 1120A. This variable plunger rod portion 1113' allows the at least one protrusion 1122A to slide relative to the plunger rod portion 1113', and to create a greater resistance when the plunger 1110a' is moved distally, than when the plunger 1110a' is moved proximally. As the plunger 1110a' is moved distally as shown in FIG. 20G, the at least one protrusion 1122A slides toward the proximal end of the plunger increasing resistance on the plunger as it moves toward the proximal end, due in part to the change in cross-sectional surface area of the plunger rod portion 1113', which serves to increase contact between the at least one protrusion 1122A and the inner surface of the housing 1109a (see FIG. 20H). Additionally, when the at least one protrusion 1122A interfaces with the protrusion interfacing surface 1111, movement of the plunger 1110a' in the distal direction may cause additional friction between the at least one protrusion 1122A and the inner surface of the housing 1109 to provide further resistance on the plunger 1110a'. In one non-limiting embodiment, a combination of distal movement of the plunger 1110a', sliding of the at least one protrusion 1122A and interfacing with the protrusion interfacing surface 1111 may increase friction to increase resistance on the distal movement of the plunger 1110a'. The friction may increase as the plunger 1110a' is moved in the distal direction due to the interaction between the components described herein.

In another embodiment 1200 shown in FIG. 21A-C, a plunger 1110b having a proximal end (not shown in FIG. 21A-C), a distal end 1120A, and a plunger rod 1113 is provided. The plunger 1110b may include one or more apertures 1118 at or near its distal end 1120A. The plunger 1110b comprises one or more vents 1120 and at least one one-way valve 1116, in one non-limiting embodiment. In a non-limiting embodiment, as shown in FIGS. 21A-C, the one-way valve may include at least one protrusion 1122B, which may include a stopper in one non-limiting embodiment, which is slidable on the plunger rod 1113. The at least one protrusion 1122B may serve to further increase the friction between the plunger 1110b and the housing during movement of the plunger 1110b in the distal direction. The plunger 1110b may include one or more vents 1120 in a portion thereof, for providing fluid flow there through. In one non-limiting embodiment, the at least one protrusion member 1122B (i.e., stopper) may serve as a valve. In a further non-limiting embodiment, the protrusion member 1122B may serve as a one-way valve as shown in FIGS. 21A-C.

Upon movement of the plunger in a distal direction as shown in FIG. 21A, the one-way valve 1116 blocks the one or more vents 1120 and prevents fluid flow therethrough, increasing the friction and pressure inside the chamber 1121 of the housing 1109. The increased pressure and friction creates a resistance on the plunger 1110b during movement of the plunger 1110b in the distal direction to simulate movement of a plunger of a medicament delivery device.

The plunger 1110b may include one or more apertures 1118, in one non-limiting embodiment. These apertures 1118 may be provided in the plunger distal end 1120A as shown in FIGS. 21A-C. In a non-limiting embodiment, the one or more apertures 1118 may provide a pathway for fluid flow there through. In a non-limiting embodiment, the fluid may include air. The housing 1109 may further include one or more fluid flow ports 1123 in a portion thereof, providing fluid flow there through. The one or more fluid flow ports 1123 provides fluid flow out of the housing 1109 when the plunger is moved in the distal direction in one non-limiting embodiment. The size and/or shape of the ports 1123, and/or the number of ports 1123 may be used to control the resistance on the plunger by increasing or decreasing the pressure within the chamber 1121.

FIG. 21C provides a cross-sectional view of FIG. 21B, wherein the plunger 1110b is moved in the proximal direction, revealing the vents 1120 in the plunger 1110b, and allowing fluid flow therethrough, as the at least one protrusion 1122B is shifted toward the distal end 1120A of the plunger so as to decrease a resistance on the movement of the plunger 1110b toward the proximal end. In FIG. 21B-C fluid flow may escape the plunger via the one or more apertures 1118, and fluid may enter the air ports 1123 of the housing 1109 during reset of the plunger 1110b toward the proximal end of the housing 1109. A differential force may be required to move the plunger 1110b in the distal direction versus the proximal direction. Movement of the plunger 1110b in the proximal direction as shown in FIG. 21B allows the plunger 1110b to be reset for a subsequent use (i.e., a subsequent training), for example. In one non-limiting embodiment, movement of the plunger 1110*b* in the proximal direction causes less resistance on the plunger 1110*b* than movement of the plunger 1110*b* in the distal direction.

A resistance on the plunger 1110*b* during movement in the distal direction simulates the movement of a plunger in a medicament-containing injection device. Injectable medicaments often vary in viscosity; consequently, the injection simulation device embodiments provided herein are configured to simulate delivery of medicaments with different viscosities to accurately simulate the injection experience for a user of the simulation device.

FIGS. 22A-D illustrate an embodiment 1300 of a plunger 1110*d* having a proximal end (not shown in FIGS. 22A-D) and a distal end 1120D. At least one protrusion member 1122D is associated with the plunger 110*d*. In the embodiment 1300 shown in FIGS. 22A-D, at least one protrusion member 1122D may include a shell 1124 for housing one or more annular members 1126. The term "annular member" as used herein, includes but is not limited to a ring-shaped member, including, for example, a garter/toroidal spring, an o-ring, or other seal, or any member having an annular-shape.

Movement of the plunger 1110*d* in a distal direction as shown by the arrow in FIG. 22A may cause the one or more annular members 1126 to contact an inner surface of the housing 1109*a* (housing not shown in FIGS. 22A-D), directly or indirectly via a shell 1124, such that a friction between the annular member(s) 1126 and/or the shell 1124 and the housing 1109 causes a resistance on the movement of the plunger 1110*d* toward the distal end movement of the plunger 1110*d* in the distal direction as shown in the embodiment of FIG. 22A increases a resistance on the plunger 1110*d*. The shell 1124 serves to limit movement of the annular member 1126 as the plunger is moved. The at least one protrusion 1122D may further include a groove 1128. Movement of the plunger 1110*d* in a proximal direction as shown in FIG. 22C allows the annular member 1126 to move toward the groove 1128, decreasing pressure of the shell 1124 and/or the annular member 1126 on the housing 1109, to reduce the friction between the protrusion member 1122D and the housing. In one non-limiting embodiment, the annular member 1126 may include a garter/toroidal spring, wherein movement of the plunger 1110*d* in a proximal direction may reduce an outer diameter of the garter/toroidal spring 1126 and decrease the friction caused thereby. FIGS. 22B and 22D demonstrate the directional movement of the annular member 1126 in FIGS. 22A and 22B, respectively.

In an alternative, non-limiting embodiment 1400, the at least one protrusion member 1122E, or alternatively, a distal portion of the plunger 1110*e* itself, may include a groove 1128 and may not include a shell 1124 as shown in the embodiment of FIG. 23A-C, for example. In this case, the annular member 1126 may move relative to the groove 1128 to increase and/or decrease the resistance on the plunger 1110*e* as the plunger 1110*e* moves in a distal direction and/or proximal direction relative to the housing 1109 as described above. In a non-limiting embodiment, an annular member interfacing surface 1129 may be provided adjacent to the groove 1128, such that proximal movement of the annular member 1126 is restricted by the annular member interfacing surface 1129 when the plunger 1110*e* is moved in a distal direction as shown in FIG. 23B. This movement increases friction by increased contact between the annular member 1126 and an inner surface 1109*a* of the housing. The friction on movement of the plunger 1110*e* in the distal direction may further be increased by contact between the at least one protrusion 1122E and the inner surface 1109*a* of the housing in another non-limiting embodiment. Movement of the plunger 1110*e* in the proximal direction as shown in FIG. 23C allows the annular member 1126 to move toward and/or into the groove 1128, decreasing the contact between the annular member 1126 and the inner surface 1109*a* of the housing, so as to reduce friction there between during movement of the plunger 1110*e* in the proximal direction. In a non-limiting embodiment, movement of the annular member 1126 away from or toward the groove includes expanding or reducing in the diameter of the annular member 1126.

In a further non-limiting embodiment, the device may be provided wherein the plunger comprises one or more grooves, and the annular member 1126 may move relative thereto as the plunger is moved in distal and proximal directions relative to the housing.

FIGS. 24A-F provide a further embodiment 1500 of a plunger 1110*c* comprising a proximal end (not shown in FIG. 24) and a distal end 1112*c*. At least one protrusion 1122C are associated with the plunger 1110*c* as shown in FIGS. 24A-F. In one non-limiting embodiment, a stopper may be associated with the plunger 110*c*, and the protrusions 1122C may be a component of the stopper. In other non-limiting embodiments, the protrusions 1122C may be a component of the plunger 1110*c*. In the embodiment 1500 provided in FIGS. 24A-F, the protrusions 1122C may further include or be associated with a flexible member 1122. In one non-limiting embodiment, the protrusion member 1122C may form the flexible member 1122, in another embodiment the flexible member 1122 may be associated with the protrusion member 1122C of the plunger 1110*c* or the stopper. In embodiments described herein, the plunger 1110*c* may be housed within a chamber 1121 of an injection simulation device housing 1109, consequently the plunger 1110*c* may be movable relative to the housing 1109. A resistance on the plunger 1110*c* may occur by interaction between at least a portion of a plunger (i.e., a protrusion 1122C or stopper) and the housing 1109 of the device in certain embodiments.

As shown in FIG. 24B, a flexible member 1122 is associated with the protrusion 1122C, and movement of the plunger 1110*c* in a distal direction may cause one or more flexible members 1122 to be displaced. In one non-limiting embodiment, displacement may include movement of the flexible member 1122 by bending or folding of the flexible member 1122 as shown in FIGS. 24B-C. This displacement causes an increase in friction between the protrusion member 1122C and the housing 1109 when the plunger 1110*c* is moved in the distal direction so as to increase a resistance on the plunger 1110*c* during movement. Further resistance may occur during distal movement of the plunger 1110*c* once the flexible member is folded over the protrusion member 1122C as shown in FIG. 24C due to the increase in contact and friction between the protrusion 1122C and the housing 1109 via the flexible member 1122, for example.

Movement of the plunger 1110*c* in the proximal direction as shown by the arrows in FIGS. 24D-F allows for a reset of the plunger 1110*c*. The movement of the plunger 1110*c* in the proximal direction, may cause the flexible member(s) 1122 to return to its original position as shown in FIG. 24E-F, decreasing the friction between the plunger 1110*c* and the housing of the injection device as the plunger is moved in the proximal direction, such that a differential force is required to move the plunger in the proximal direction than that which is required to move the plunger in the distal direction.

FIG. 25B is a cross-sectional view of the side view of FIG. 25A, and FIG. 25D is a cross sectional view of the side view of FIG. 25C of a further embodiment of an injection simulation device. In the non-limiting injection simulation device embodiment 1600 shown in FIGS. 25A-D, a housing 1109 defining a channel 1121 is provided, wherein a plunger 1110 having a proximal end 1120B and a distal end 1120A is movable relative to the channel 1121. The plunger comprises a plunger rod and at least one protrusion 1114 that interfaces with the housing 1109. The housing 1109 may include a simulated needle 1140 associated with a distal end of the housing, in one non-limiting embodiment. In a further non-limiting embodiment, the simulated needle 1140 may be retractable relative to the housing as shown in FIG. 25. The retractable simulated needle 1140 may be used to simulate the needle of an injection device, and may be used to train a user to deliver an injection. The simulated needle 1140 may be associated with a biasing member 1142, such that it may be retracted and extended relative to the housing 1109. The simulated needle 1140 has a proximal end and a distal end, the distal end for associating with a target surface of a user. The distal end comprising a profile such that use of the device 1600 will not puncture the target surface of a user. The proximal end of the simulated needle 1140 may include or be associated with a valve closing member 1138, configured to associate with a valve 1136. In one non-limiting embodiment, upon full retraction of the simulated needle 1140, the valve closing member 1138 prevents fluid flow through the valve 1136. In the embodiment 1600, retraction of the simulated needle as shown in FIG. 25C resulting in an interface between valve 1136 and valve closing member 1138 increases the pressure within the chamber 1121, consequently, blocking of the valve 1136 with the valve closing member 1138 causes an increase in resistance on the movement of the plunger 1110 in the distal direction (i.e., toward the distal end of the housing 1109) as shown in FIGS. 25C-25D. A fluid flow port 1123 may be provided in the housing 1109 as shown in FIG. 25, providing for fluid flow there through in some non-limiting embodiments, so as to allow for movement of the plunger 1110 within the housing 1109.

As illustrated in the embodiments of FIG. 25A-25D, a surface treatment or surface texture region 1195 may be applied to an inner surface of the housing 1109. the surface texture region 1195 may be provided on an inner surface of the housing, or on a portion of the plunger and/or the stopper or protrusion member in some embodiments, or a combination thereof. The surface texture region 1195 may increase the coefficient of friction during movement of the plunger relative to the housing. The surface texture region may be included in any of the embodiments provided herein. In some embodiments, the surface texture region(s) may include a higher average roughness (Ra) relative to other non-surface texture regions.

Figure 27:
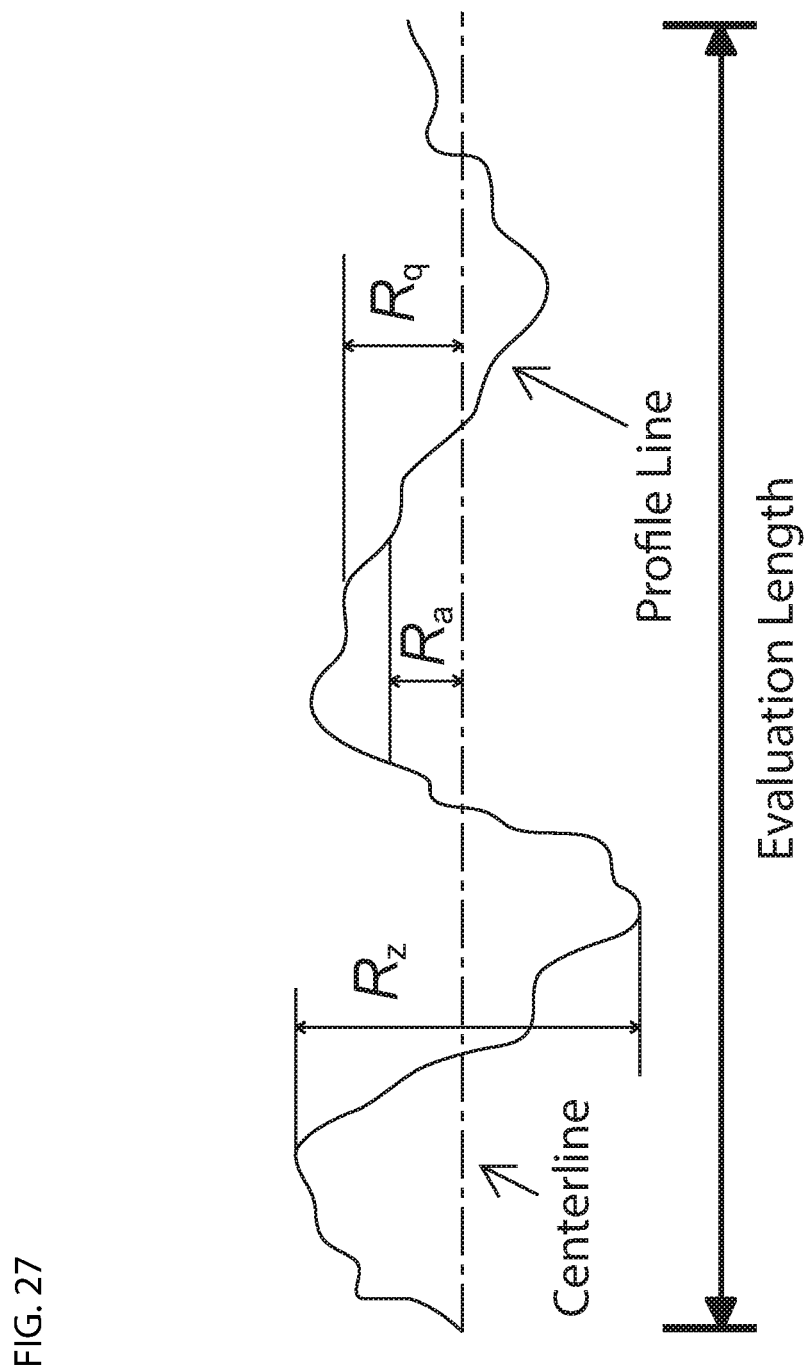
FIG. 27 presents a sample graph showing the relationship between the Rz, Rq and Ra values.

Non-limiting examples of surface texture regions described herein may include a surface texture profile comprising a number of peaks and valleys, wherein the peak to valley distance (Rz) is the largest distance between the highest and lowest points of the profile for a given evaluation length. The average roughness (Ra) may be calculated as the average distance of the profile from the centerline and the root-mean-square (rms) roughness Rq is taken as the root-mean-square of the profile distance from the centerline. See, for example, the sample graph showing the relationship between the Rz, Rq and Ra values provided in FIG. 27.

Controlling the surface finish of selected regions of a core pin used in the injection molding process to manufacture the device according to one embodiment, can be used to vary the surface roughness along the length of the inner diameter of the produced part. Varying the surface finish of portions of the core pin can be accomplished through selective masking and secondary finishing processes. There is a strong correlation between increased surface roughness and an increased coefficient of friction in dry sliding wear. Varying the surface roughness of selected regions along the length of the vial can therefore be used to vary the force required to move the plunger along its length. The level of achievable surface finish variation along the length of the vial will vary depending on the degree of draft angle of the inner diameter. The surface finish of portions of the vial can be varied from approximately 0.001 Ra (μm) to 25.0 Ra (μm), in other embodiments, the Ra value may range from 0.012 μm to 18.0 μm, and in some embodiments, from approximately 0.012 Ra (μm) to 6.35 Ra (μm). These varying Ra values may occur through the selective application of finishing methods, for example.

In some examples, ranges for Rq may include between 0.001 μm and 0.1 μm, in some embodiments Rq value may range between 0.012 μm and 0.025 μm. In other embodiments, Rq may range between 0.013 μm and 0.027 μm.

Figure 26C:
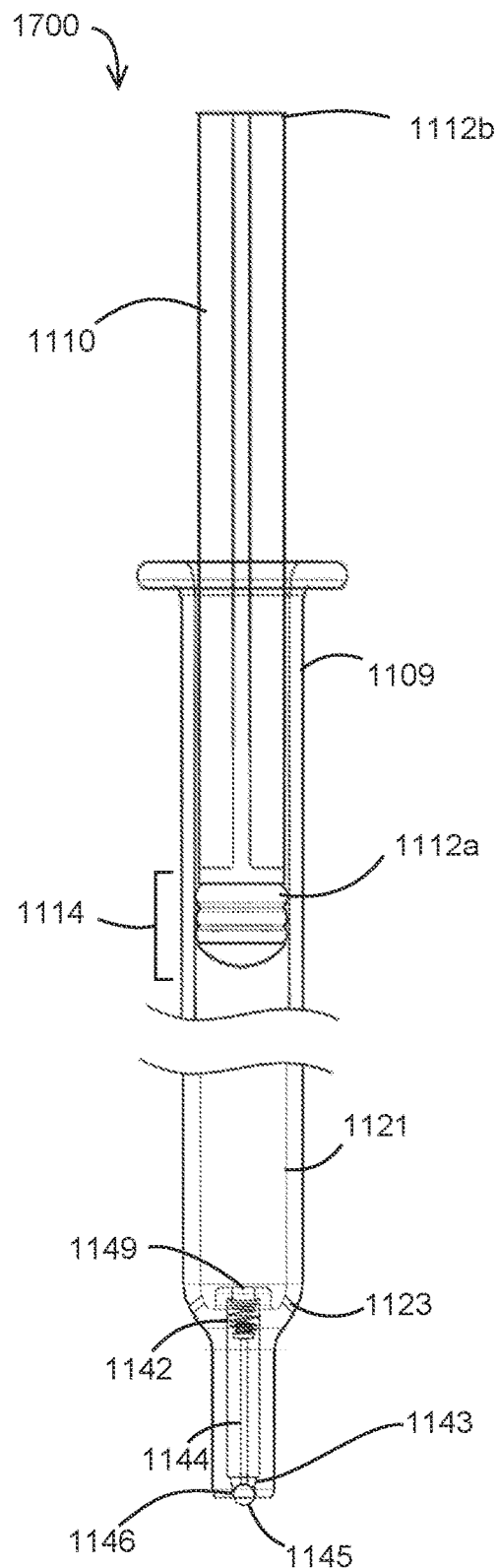
FIG. 26C is a partial cutaway view of the embodiment of the device shown in FIG. 26A.
Figure 26D:
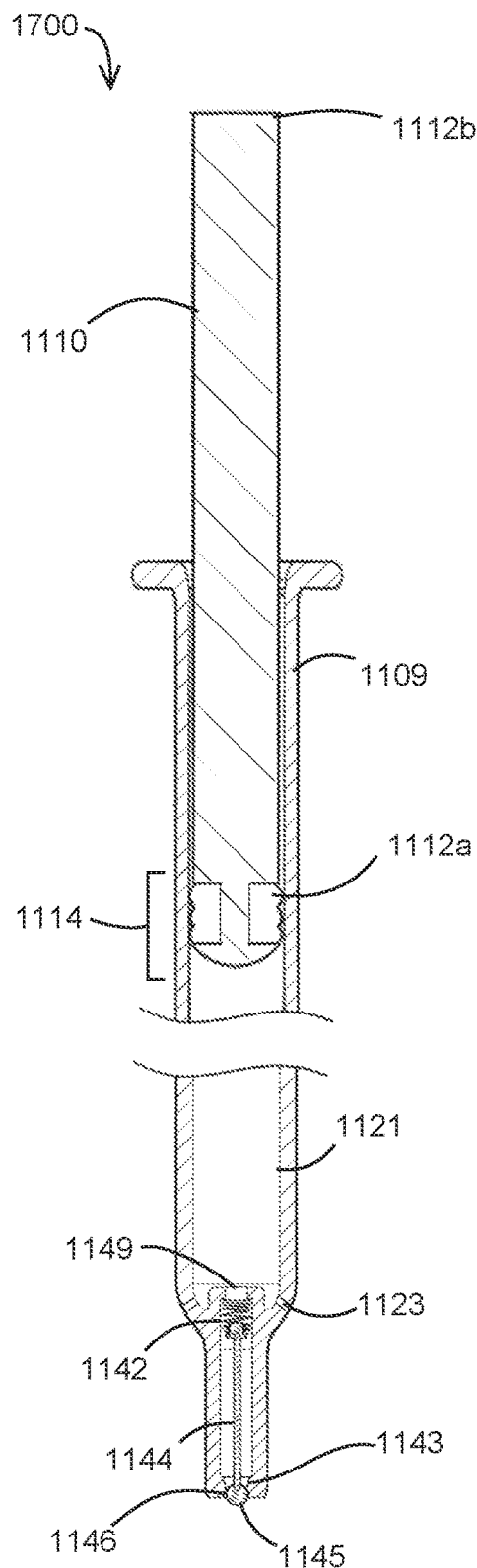
FIG. 26D is a cross sectional view of the embodiment of the device shown in FIG. 26C.

FIGS. 26A-26D illustrate a further non-limiting embodiment of an injection simulation device 1700 for simulating plunger resistance of an injection device. The embodiment 7100 includes a housing 1109 defining a channel 1121, and a plunger 1110 for movement relative to the channel 1121. The plunger 1110 includes a proximal end 1120B and a distal end 1120A and a protrusion 1114 at the distal end for interfacing with the housing 1109. FIG. 26B is a cross sectional view of the device as shown in FIG. 26A, and FIG. 26D provides a cross sectional view of the device as shown in FIG. 26C. A retractable simulated needle 1144 is shown, the simulated needle 1144 is retractable relative to the housing 1109. The simulated needle 1144 having a proximal end and a distal end, and a distal end component 1145 associated with its distal end of the simulated needle in one non-limiting embodiment. The distal end of the simulated needle 1144 for contacting a target surface of a user during use of the device 1700. The proximal end of the simulated needle 1144 may include a distal end component receiving notch 1146 for receiving the distal end component 1145. The distal end component receiving notch 1146 may be complimentary to the distal end component, such that when the distal end component 1145 interfaces with the distal end component receiving notch 1146, fluid flow through the distal end aperture 1143 is restricted. The interface between the distal end component receiving notch 1146 and the distal end component 1145 as shown in FIGS. 26C-D increases pressure in the chamber 1121, to increase a resistance on the plunger 110 during movement in the distal direction. This allows simulation of the resistance sensed during movement of a plunger in a medicament-containing injection device. The interface between the distal end component 1145 and the distal end component receiving notch 1146 serves to block the valve 1149 of the housing 1109, preventing fluid flow from passing therethrough. A biasing member 1142 is associated with the simulated needle 1144, the biasing member 1142 configured to extend the simulated needle 1144, in one non-limiting embodiment, when the force on the distal end of the simulated needle 1144 is removed or reduced.

Consequently, the embodiment 1700 of the injection simulation device provides a multi-step approach to training a user for using an injection device, wherein the simulated needle 1144 must be retracted before the plunger is actuated (i.e., moved toward the distal end), to simulate an injection delivery device. An injection delivery device as mentioned herein includes a medicament containing injection device, and more specifically, in non-limiting embodiments, a needle-containing medicament-containing injection device such as a prefilled syringe, for example.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. As a non-limiting example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 7.

It should be borne in mind that all patents, patent applications, patent publications, technical publications, scientific publications, and other references referenced herein are hereby incorporated by reference in this application in order to more fully describe the state of the art to which the present invention pertains.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While one or more embodiments of the present invention have been shown and described herein, such embodiments are provided by way of example only. Variations, changes and substitutions may be made without departing from the invention herein. Accordingly, it is intended that the invention be limited only by the spirit and scope of the appended claims. The teachings of all references cited herein are incorporated in their entirety to the extent not inconsistent with the teachings herein.

What is claimed is:

1. An injection simulation device, comprising:
   a housing defining a channel, the housing comprising a proximal end and a distal end;
   a plunger comprising a plunger rod having a proximal end and a distal end and a stopper disposed at the distal end of the plunger rod, the plunger movable proximally and distally within the channel; and
   a friction feature associated with the housing, the friction feature for interfacing with the plunger rod;
   wherein the plunger moves in a distal direction relative to the housing to simulate medicament delivery and in a proximal direction to reset the injection simulation device, wherein the friction feature optionally causes differential resistance on the plunger rod, when the plunger rod moves in either the distal or proximal direction.

2. The injection simulation device of claim 1, wherein a force on the proximal end of the plunger moves the plunger in a distal direction, such that the force on the plunger proximal end to move the plunger distally simulates a force profile of plunger movement of an injection device required to deliver medicament there from.

3. The injection simulation device of claim 2, wherein the simulated force profile comprises a breakaway force characterized by an initial first resistance followed by a glide force with a second resistance, wherein the first resistance is greater than the second resistance.

4. The injection simulation device of claim 1, further comprising a flange portion, wherein the plunger is slidable relative to the flange portion and wherein the flange portion comprises the friction feature, such that movement of the plunger relative to the flange portion causes the differential resistance on the plunger rod movement.

5. The injection simulation device of claim 4, wherein the flange portion comprises an opening, said friction feature comprising one or more flap members extending into the opening, wherein the one or more flap members are configured to interface with the plunger rod as the plunger slides relative to the flange portion.

6. The injection simulation device of claim 5, wherein at least a portion of the one or more flap members comprises a flexible material, such that distal movement of the plunger increases a resistance on plunger movement, and proximal movement of the plunger causes the at least a portion of the one or more flap members to flex, releasing a surface area contact between the plunger rod and the one or more flap members, decreasing a resistance on the proximal plunger movement.

7. The injection simulation device of claim 5, wherein each of the one or more flap members comprises at least a first layer and a second layer, the first layer comprising the flexible material, and the second layer comprising a rigid material, such that distal plunger movement prevents flexing of the one or more flap members, and increases a resistance on the plunger rod, and the proximal plunger movement causes at least the first layer to flex, reducing a resistance on the plunger rod during proximal plunger movement.

8. The injection simulation device of claim 1, wherein the plunger rod comprises a cross-shaped profile; wherein the plunger rod comprises a plunger rod core and a plurality of plunger cross members, wherein each of the plurality of plunger cross members comprises a width dimension and a height dimension; and wherein at least one of the plurality of plunger cross members comprises a larger height dimension at the proximal end of the plunger and a smaller height dimension at the distal end of the plunger.

9. The injection simulation device of claim 8, wherein at least one of the plurality of plunger cross members comprises a smaller height dimension at the proximal end of the plunger rod and a larger height dimension at the distal end of the plunger rod; wherein at least one of the plurality of plunger cross members comprises a larger width dimension at the proximal end of the plunger rod and a smaller width dimension at the distal end of the plunger rod; or wherein at least one of the plurality of plunger cross members comprises a smaller width dimension at the proximal end of the plunger rod and a larger width dimension at the distal end of the plunger rod.

10. The injection simulation device of claim 1, wherein the plunger rod comprises a first cross-sectional surface area adjacent to the proximal end, and a second cross-sectional surface area adjacent to the distal end.

11. The injection simulation device of claim 10, wherein the first cross-sectional surface area is greater than the second cross-sectional surface area; or wherein the first cross-sectional surface area is substantially equal to the second cross-sectional surface area; or wherein the first cross-sectional surface area is less than the second cross-sectional surface area.

12. The injection simulation device of claim 10, wherein the plunger rod further comprises a third cross-sectional surface area between the first cross-sectional surface area, and the second cross sectional surface area.

13. The injection simulation device of claim 8, further comprising a resistance nodule disposed on the plunger, on the housing, or on both the plunger and the housing to simulate a breakaway force as the plunger is moved distally.

14. The injection simulation device of claim 8, wherein the plunger rod comprises a first cross member, a second cross member, a third cross member, and a fourth cross member, wherein at least one of the cross members comprises a first width at the proximal end of the plunger rod, and the at least one cross member comprises a second width at the distal end of the plunger rod, wherein the first width is larger than the second width.

15. The injection simulation device of claim 10, wherein the cross sectional surface area comprises a first width F and a second width D, wherein the first width F at the proximal end of the plunger rod is substantially equivalent to the first width F at the distal end of the plunger rod; wherein the second width D at the proximal end of the plunger rod is substantially equivalent to the second width D at the distal end of the plunger rod; or wherein the second width D at the proximal end of the plunger rod is greater than the second width D at the distal end of the plunger rod.

16. The injection simulation device of claim 1, wherein the housing further comprises an aperture and wherein the aperture is configured to receive a portion of a clip member.

17. The injection simulation device of claim 4, wherein the plunger rod comprises a first cross-sectional surface area at the proximal end and a second cross-sectional surface area at the distal end, and wherein the flange portion comprises a pocket for maintaining the frictional feature, wherein the frictional feature comprises an annular member, the annular member configured to surround the plunger rod and an interface between the plunger rod and the annular member increases a resistance on the plunger rod as it is moved distally; and wherein the first cross-sectional surface area is greater than the second cross-sectional surface area of the plunger rod.

18. The injection simulation device of claim 1, wherein the friction feature comprises an annular member disposed between the plunger rod and the housing, such that resistance on the plunger rod is increased during distal movement of the plunger.

* * * * *